(12) United States Patent
Jia

(10) Patent No.: US 11,235,015 B2
(45) Date of Patent: Feb. 1, 2022

(54) ANTIVIRAL TRADITIONAL CHINESE MEDICINE COMPOSITION AND PREPARATION METHOD AND USE THEREOF

(71) Applicant: Hongzhang Jia, Beijing (CN)

(72) Inventor: Hongzhang Jia, Beijing (CN)

( * ) Notice: Subject to any disclaimer, the term of this patent is extended or adjusted under 35 U.S.C. 154(b) by 65 days.

(21) Appl. No.: 16/613,392

(22) PCT Filed: May 15, 2018

(86) PCT No.: PCT/CN2018/086848
§ 371 (c)(1),
(2) Date: Nov. 13, 2019

(87) PCT Pub. No.: WO2018/210228
PCT Pub. Date: Nov. 22, 2018

(65) Prior Publication Data
US 2020/0164015 A1 May 28, 2020

(30) Foreign Application Priority Data

May 16, 2017 (CN) .......................... 201710346946.7

(51) Int. Cl.
*A61K 36/288* (2006.01)
*A61P 31/16* (2006.01)
*A61K 36/27* (2006.01)
*A61K 36/284* (2006.01)
*A61K 36/488* (2006.01)
*A61K 36/605* (2006.01)
*A61K 36/815* (2006.01)
*A61K 36/898* (2006.01)
*A61K 36/904* (2006.01)

(52) U.S. Cl.
CPC ............ *A61K 36/288* (2013.01); *A61K 36/27* (2013.01); *A61K 36/284* (2013.01); *A61K 36/488* (2013.01); *A61K 36/605* (2013.01); *A61K 36/815* (2013.01); *A61K 36/898* (2013.01); *A61K 36/904* (2013.01); *A61P 31/16* (2018.01); *A61K 2236/331* (2013.01); *A61K 2236/333* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| CN | 1425392 A | 6/2003 |
|---|---|---|
| CN | 1435241 A | 8/2003 |
| CN | 1634533 A | 7/2005 |
| CN | 101112409 A | 1/2008 |
| CN | 101518592 A | 9/2009 |
| CN | 101537154 A | * 9/2009 |
| CN | 102000156 A | * 4/2011 |
| CN | 102451412 A | 5/2012 |
| CN | 102670684 A | 9/2012 |
| CN | 102861208 A | 1/2013 |
| CN | 103099838 A | 5/2013 |
| CN | 103169903 A | 6/2013 |
| CN | 103494945 A | 1/2014 |
| CN | 103749818 A | 4/2014 |
| CN | 104186779 A | 12/2014 |
| CN | 104225175 A | 12/2014 |
| CN | 104721388 A | * 6/2015 |
| CN | 105770644 A | 7/2016 |
| CN | 107184886 A | 9/2017 |
| JP | 07118161 A | 5/1995 |
| WO | 2015191891 A1 | 12/2015 |

OTHER PUBLICATIONS

CN-101537154-A translated docs (Year: 2009).*
CN-102000156-A translated docs (Year: 2011).*
CN-104721388-A translated docs (Year: 2015).*
The Office Action issued by the Japanese Patent Office dated Nov. 17, 2020 for the Japanese Patent Application No. 2020-514317.
The Office Action issued by the China National Intellectual Property Administration (CNIPA) dated Nov. 6, 2017 for the Chinese Patent Application No. 201710346946.7.
The cited reference (Nonpatent 1) in the Office Action issued by the CNIPA dated Nov. 6, 2017 for the Chinese Patent Application No. 201710346946.7, last page, first reference.
The cited reference (Nonpatent 2) in the Office Action issued by the CNIPA dated Nov. 6, 2017 for the Chinese Patent Application No. 201710346946.7, last page, second reference.
The cited reference (Nonpatent 3) in the Office Action issued by the CNIPA dated Nov. 6, 2017 for the Chinese Patent Application No. 201710346946.7, last page, third reference.
International Search Report and Written Opinion for PCT/CN2018/086848, dated Aug. 17, 2018.
The Second Office Action issued by the Japanese Patent Office dated Jun. 15, 2021 for the Japanese Patent Application No. 2020-514317.
Extended European Search Report for European Patent Application No. 18802679.3, dated May 7, 2021.

(Continued)

*Primary Examiner* — Susan Hoffman
*Assistant Examiner* — Jacob A Boeckelman
(74) *Attorney, Agent, or Firm* — Maschoff Brennan; Brent A. Johnson; Yuefen Zhou

(57) ABSTRACT

An antiviral traditional Chinese medicine composition, a preparation method therefor and a pharmaceutical application thereof. The composition uses Herba Taraxaci, Radix Stemonae, Pseudobulbus Cremastrae Seu Pleiones, Radix Puerariae, Rhizoma Atractylodis Macrocephalae, and Radix Cynanchi Atrati as main active pharmaceutical ingredients, may also optionally and additionally use Cortex Lycii Radicis and Cortex Mori as active pharmaceutical ingredients, and is prepared into a pharmaceutically acceptable dosage form according to needs. The medicine composition is effective against influenza A virus, H1N1, H7N7 and H9N2 viruses, Zika virus, dengue virus I, dengue virus II, and Chikungunya virus.

12 Claims, 8 Drawing Sheets

(56) References Cited

OTHER PUBLICATIONS

Database WPI Week 201520 Thomson Scientific, London, GB; AN 2015-113723 XP002802495, & CN 104 225 175 A (Tianjin Junhexin Sci & Technology Dev Co) Dec. 24, 2014, Abstract.
Database TCM [Online] SIPO; Jan. 9, 2013, Wang Jikun: "A kind of Chinese medicine compound with effects of resisting inflammation and virus", XP002802496, Database accession No. CN-201210382638-A, Abstract.
Database WPI Week 201314 Thomson Scientific, London, GB; AN 2013-A19765 XP002802497, & CN 102 670 684 A (Chinese Acad Sci Shanghai Biological Sci) Sep. 19, 2012, Abstract.
Database WPI Week 200618 Thomson Scientific, London, GB; AN 2006-165336 XP002802498, & CN 1 634 533 A (Hu S) Jul. 6, 2005, Abstract.
Database WPI Week 200363 Thomson Scientific, London, GB; AN 2003-664166 XP002802499, & CN 1 425 392 A (Zhuhai Jinsha Hunan Pharm Co Ltd) Jun. 25, 2003, Abstract.
Database WPI Week 201246 Thomson Scientific, London, GB; AN 2012-G20325 XP002802500, & CN 102 451 412 A (Zhao Q) May 16, 2012, Abstract.

\* cited by examiner

ANTIVIRAL TRADITIONAL CHINESE MEDICINE COMPOSITION AND PREPARATION METHOD AND USE THEREOF

CROSS REFERENCE TO RELATED APPLICATIONS

The present application is a national phase of International Application No. PCT/CN2018/086848, filed May 15, 2018, which claims priority to Chinese Patent Application No. 201710346946.7 filed May 16, 2017, both of which are incorporated by reference herein in their entirety.

TECHNOLOGY FIELD

The present disclosure relates to the field of drug research and development and relates to a Traditional Chinese Medicine composition with inhibitory activity against a wide range of viruses responsible for acute infectious diseases; in particular, the present disclosure relates to a Traditional Chinese Medicine composition which is effective against viruses such as influenza A virus, Zika virus, dengue virus and chikungunya virus, and the preparation and application of said composition.

BACKGROUND

Influenza A virus, Zika virus (ZIKV), dengue virus (DEN), and chikungunya virus (CHIKV) pose a great threat to human health due to their widespread and rapid transmission via mosquitoes or through respiratory tract and their highly infectious nature as well as the high mortality rate caused by them. These viruses have been extensively studied. Taxonomically, influenza A virus belongs to the family of Orthomyxoviridae; Zika virus and dengue virus belong to the family of Flaviviridae and the genus of Flavivirus; chikungunya virus belongs to the family of Togaviridae and the genus of alphavirus. Prevention and treatment of influenza A virus, Zika virus, dengue virus, and chikungunya virus remains as a worldwide challenge. There are currently no effective drugs and satisfactory clinical treatments for the prevention and treatment of the acute infectious diseases caused by these viruses.

1. Anti-influenza drugs for clinical use against type A virus mainly include M2 ion channel inhibitors and neuraminidase inhibitors. The adverse effects of amantadine and rimantadine include neurotoxicity, and drug-resistant strains would generally appear 2 to 3 days after treatment. The adverse effects of oseltamivir are mainly discomfort in digestive tract and side effects in respiratory and central nervous systems; and the Global Influenza Surveillance Network conducted systematic monitoring with the support of the WHO Collaborating Centre and other laboratories and confirmed the drug resistance of influenza A H1N1 virus. Zanamivir is administered by oral inhalation, and the powder is directly inhaled to act on the viral replication site (in the respiratory tract). Local administration can become inconvenient to patients, and may induce bronchospasm and thus is not recommended for patients suspicious of lung diseases. It is difficult to prevent and treat influenza A virus due to its high variability. It is thus very necessary to develop new treatments with high efficiency and low toxicity.

2. Effective vaccine, specific antiviral drug or treatment for Zika virus, which is an RNA virus, has not yet been developed.

3. No effective antiviral drugs have been developed for dengue virus or chikungunya virus infection.

Traditional Chinese Medicine (TCM) has been used in China for thousands of years. Generally, TCM is based on many chemical components in an herbal preparation that interact and act simultaneously through multiple molecular targets and cellular mechanisms. These multiple components serve various functions; some may be responsible for efficacy while others may decrease toxicity or increase bioavailability. Currently, mixtures of botanical extracts have been widely used throughout the world for the management of disease and are gaining increased acceptance in Western countries.

Attempts have been made to develop antiviral Traditional Chinese Medicine compositions; however, current researches are still in early stage with few convincing experimental data.

Chinese Patent Application No. 201610226648.X, entitled "Traditional Chinese Medicine For Repairing Flavivirus Infected Blood Cells", discloses a Traditional Chinese Medicine for repairing Flavivirus infected blood cells, which is said to be effective for diseases caused by dengue virus, Zika virus, etc.; however, no experimental data, especially those for antiviral effects, are provided in the description.

Chinese Patent Application No. 201610424049.9, entitled "Traditional Chinese Medicine Composition for Treating Dengue Fever", discloses a Traditional Chinese Medicine composition for treating dengue fever, but does not provide any data on therapeutic effects.

Chinese Patent Application No. 201510408826.6 entitled "Traditional Chinese Medicine Preparation for Treating Dengue Fever and Preparation Method Thereof" discloses a Traditional Chinese Medicine preparation for treating dengue fever, and the description discloses a comparative test to prove that the Traditional Chinese Medicine preparation has certain therapeutic effects; however, no data on antiviral activity are disclosed.

Chinese Patent Application No. 201410607204.1, entitled "Preparation Method of Traditional Chinese Medicine Preparation for Treating Dengue Fever", discloses a Traditional Chinese Medicine preparation for treating dengue fever and preparation method thereof, and the description provides drug toxicity data and clinical data to prove that the Traditional Chinese Medicine preparation has certain therapeutic effects; however, no data on antiviral activity are disclosed.

DETAILED DESCRIPTION

It is thus desirable to develop a pharmaceutical composition with antiviral activity. In particular, there is an urgent need for a pharmaceutical composition that is effective against acute infectious diseases caused by viruses such as influenza A virus, Zika virus, dengue virus, chikungunya virus, and the like.

The inventor found unexpectedly that a Traditional Chinese Medicine composition prepared from Herba Taraxaci, Radix Stemonae, Pseudobulbus Cremastrae Seu Pleiones, Radix Puerariae, Rhizoma Atractylodis Macrocephalae, and Radix Cynanchi Atrati as main raw materials have significant antiviral effects; in particular, such composition has broad-spectrum and highly efficient antiviral activity against viruses responsible for acute infectious diseases such as influenza A virus, Zika virus, dengue virus and chikungunya virus.

The inventor discovered by conducting a large number of in vivo and in vitro experiments that the Traditional Chinese Medicine composition prepared from Herba Taraxaci, Radix Stemonae, Pseudobulbus Cremastrae Seu Pleiones, Radix Puerariae, Rhizoma Atractylodis Macrocephalae, and Radix Cynanchi Atrati as main raw materials have significant antiviral effects against viruses from Orthomyxoviridae, Flaviviridae, and Togaviridae families, especially viruses from Flavivirus genus of Flaviviridae, Alphavirus genus of Togaviridae, and Influenza A virus genus of Orthomyxoviridae, such as influenza A virus (including H1N1, H7N7 and H9N2, etc.), Zika virus, dengue virus (including dengue type I and dengue type II virus), chikungunya virus, etc.

Therefore, in particular embodiments, the present disclosure provides an antiviral Traditional Chinese Medicine composition prepared from Herba Taraxaci, Radix Stemonae, Pseudobulbus Cremastrae Seu Pleiones, Radix Puerariae, Rhizoma Atractylodis Macrocephalae, and Radix Cynanchi Atrati as main raw materials.

The raw materials used in the composition of the present disclosure are commonly used herbs, and are described in detail in the "Chinese Pharmacopoeia" and "Chinese Materia Medica", and can be easily obtained commercially. There is no particular limitation on the origins of these herbal materials, provided that they comply with relevant national standards and regulations.

The term "Herba Taraxaci" used herein refers to the dried whole grass of *Taraxacum mongolicum* Hand.-Mazz, *Taraxacum sinicum* Kitag. or other plants from the same genus in the family of Compositae.

The term "Radix Stemonae" used herein refers to the dried root of *Stemona sessilifolia* (Miq.) Miq., *Stemona japonica* (BI.) Miq. or *Stemona tuberosa* Lour. in the family of Stemonaceae.

The term "Pseudobulbus Cremastrae Seu Pleiones", also known as *Cremastra appendiculata*, used herein refers to the dried pseudobulb of *Cremastra appendiculata* (D.Don) Makino in the family of Orchidaceae.

The term "Radix Puerariae" used herein refers to the dried root of *Pueraria lobata* (Willd.) Ohwi or *Pueraria thomsonii* Benth. in the family of Leguminosae.

The term "Rhizoma Atractylodis Macrocephalae" used herein refers to the dried root of *Atractylodes macrocephala* Koidz. in the family of Compositae.

The term "Radix Cynanchi Atrati" used herein refers to the dried roots and rhizomes of *Cynanchum atratum* Bge. or *Cynanchum versicolor* Bge. in the family of Asclepiadaceae.

It has been found that the Traditional Chinese Medicine composition prepared from Herba Taraxaci, Radix Stemonae, Pseudobulbus Cremastrae Seu Pleiones, Radix Puerariae, Rhizoma Atractylodis Macrocephalae, and Radix Cynanchi Atrati with weight ratios within the following range achieves good antiviral effect: Herba Taraxaci 30-70 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight.

Therefore, in particular embodiments, the present disclosure provides an antiviral Traditional Chinese Medicine composition comprising the following raw materials: Herba Taraxaci 30-70 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight; wherein preferred amounts of the raw materials are as follows:

Herba Taraxaci: preferably 30-60 parts by weight, more preferably 35-55 parts by weight, most preferably 40-50 parts by weight;

Radix Stemonae: preferably 25-35 parts by weight, most preferably 25-30 parts by weight;

Pseudobulbus Cremastrae Seu Pleiones: preferably 25-35 parts by weight, most preferably 25-30 parts by weight;

Radix Cynanchi Atrati: preferably 20-45 parts by weight, more preferably 20-40 parts by weight, most preferably 25-35 parts by weight;

Radix Puerariae: preferably 20-45 parts by weight, more preferably 20-40 parts by weight, most preferably 25-35 parts by weight;

Rhizoma Atractylodis Macrocephalae: preferably 20-55 parts by weight, more preferably 20-50 parts by weight, most preferably 30-40 parts by weight.

It will be understood by those skilled in the art that any one of the above preferred ranges of each of the above raw materials can be combined with any one of the preferred ranges of other above raw materials, and these combinations are all considered as embodiments of the present invention. The present disclosure therefore provides the following embodiments.

In certain preferred embodiments, the present disclosure provides an antiviral Traditional Chinese Medicine composition comprising the following raw materials: Herba Taraxaci 30-60 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight.

In other preferred embodiments, the present disclosure provides an antiviral Traditional Chinese Medicine composition comprising the following raw materials: Herba Taraxaci 30-60 parts by weight, Radix Stemonae 25-35 parts by weight, Pseudobulbus Cremastrae Seu Pleiones 25-35 parts by weight, Radix Cynanchi Atrati 20-45 parts by weight, Radix Puerariae 20-45 parts by weight, and Rhizoma Atractylodis Macrocephalae 20-50 parts by weight.

In other preferred embodiments, the present disclosure provides an antiviral Traditional Chinese Medicine composition comprising the following raw materials: Herba Taraxaci 30-60 parts by weight, Radix Stemonae 25-35 parts by weight, Pseudobulbus Cremastrae Seu Pleiones 25-35 parts by weight, Radix Cynanchi Atrati 20-40 parts by weight, Radix Puerariae 20-40 parts by weight, and Rhizoma Atractylodis Macrocephalae 20-50 parts by weight.

In other preferred embodiments, the present disclosure provides an antiviral Traditional Chinese Medicine composition comprising the following raw materials: Herba Taraxaci 30-60 parts by weight, Radix Stemonae 25-35 parts by weight, Pseudobulbus Cremastrae Seu Pleiones 25-35 parts by weight, Radix Cynanchi Atrati 25-35 parts by weight, Radix Puerariae 25-35 parts by weight, and Rhizoma Atractylodis Macrocephalae 30-40 parts by weight.

In other preferred embodiments, the present disclosure provides an antiviral Traditional Chinese Medicine composition comprising the following raw materials: Herba Taraxaci 35-55 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight.

In other preferred embodiments, the present disclosure provides an antiviral Traditional Chinese Medicine composition comprising the following raw materials: Herba Taraxaci 35-55 parts by weight, Radix Stemonae 25-35 parts by weight, Pseudobulbus Cremastrae Seu Pleiones 25-35 parts by weight, Radix Cynanchi Atrati 20-45 parts by weight, Radix Puerariae 20-45 parts by weight, and Rhizoma Atractylodis Macrocephalae 20-50 parts by weight.

In other preferred embodiments, the present disclosure provides an antiviral Traditional Chinese Medicine composition comprising the following raw materials: Herba Taraxaci 35-55 parts by weight, Radix Stemonae 25-35 parts by weight, Pseudobulbus Cremastrae Seu Pleiones 25-35 parts by weight, Radix Cynanchi Atrati 20-40 parts by weight, Radix Puerariae 20-40 parts by weight, and Rhizoma Atractylodis Macrocephalae 20-50 parts by weight.

In other preferred embodiments, the present disclosure provides an antiviral Traditional Chinese Medicine composition comprising the following raw materials: Herba Taraxaci 35-55 parts by weight, Radix Stemonae 25-35 parts by weight, Pseudobulbus Cremastrae Seu Pleiones 25-35 parts by weight, Radix Cynanchi Atrati 25-35 parts by weight, Radix Puerariae 25-35 parts by weight, and Rhizoma Atractylodis Macrocephalae 30-40 parts by weight.

In other preferred embodiments, the present disclosure provides an antiviral Traditional Chinese Medicine composition comprising the following raw materials: Herba Taraxaci 40-50 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight.

In other preferred embodiments, the present disclosure provides an antiviral Traditional Chinese Medicine composition comprising the following raw materials: Herba Taraxaci 40-50 parts by weight, Radix Stemonae 25-35 parts by weight, Pseudobulbus Cremastrae Seu Pleiones 25-35 parts by weight, Radix Cynanchi Atrati 20-45 parts by weight, Radix Puerariae 20-45 parts by weight, and Rhizoma Atractylodis Macrocephalae 20-50 parts by weight.

In other preferred embodiments, the present disclosure provides an antiviral Traditional Chinese Medicine composition comprising the following raw materials: Herba Taraxaci 40-50 parts by weight, Radix Stemonae 25-35 parts by weight, Pseudobulbus Cremastrae Seu Pleiones 25-35 parts by weight, Radix Cynanchi Atrati 20-40 parts by weight, Radix Puerariae 20-40 parts by weight, and Rhizoma Atractylodis Macrocephalae 20-50 parts by weight.

In other preferred embodiments, the present disclosure provides an antiviral Traditional Chinese Medicine composition comprising the following raw materials: Herba Taraxaci 40-50 parts by weight, Radix Stemonae 25-35 parts by weight, Pseudobulbus Cremastrae Seu Pleiones 25-35 parts by weight, Radix Cynanchi Atrati 25-35 parts by weight, Radix Puerariae 25-35 parts by weight, and Rhizoma Atractylodis Macrocephalae 30-40 parts by weight.

In other preferred embodiments, the present disclosure provides an antiviral Traditional Chinese Medicine composition, wherein the amount of each of the raw material is, for example, as described in the Examples provided in the present disclosure, and the amount of each of the raw material can be any amount which lies within the range defined by a variation of up to about ±16% of the amount disclosed in the Examples, more preferably the amount of each of the raw material can be any amount which lies within the range defined by a variation of up to about ±15%, ±12%, ±10%, ±8%, ±5%, ±4%, ±3% or ±2% of the amount disclosed in the Examples.

It has been found that the antiviral activity of the Traditional Chinese Medicine composition according to the present disclosure is excellent when the amount of each raw material is within the above preferred ranges.

The antiviral Traditional Chinese Medicine composition of the present disclosure can be provided in the form of a combination of each raw material (for example, a medicine kit), and the composition can be taken by a patient via oral administration after decocting the prescribed herbs with added water according to conventional methods known in the field of Traditional Chinese Medicine. However, preferably, the antiviral Traditional Chinese Medicine composition of the present disclosure can be processed into a herbal extract composition (e.g., a premix) by modern processing methods so that it can be administrated to a patient directly with more convenience.

Therefore, in certain particular embodiments, the present disclosure provides an antiviral Traditional Chinese Medicine composition comprising an extract of the raw materials, i.e., Herba Taraxaci, Radix Stemonae, Pseudobulbus Cremastrae Seu Pleiones, Radix Puerariae, Rhizoma Atractylodis Macrocephalae, and Radix Cynanchi Atrati, wherein the amount of each raw material is: Herba Taraxaci 30-70 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight, and the preferred amounts of each raw material is as described above.

The term "extract" used herein refers to an extract obtained by extracting herbal raw materials using water or an organic solvent. Preferably, extract obtained by using solvent such as water, a C1-C6 alcohol, hexane, chloroform, methyl acetate, diethyl ether, etc. can be used, and more preferably the solvent is selected from the group consisting of water, methanol, ethanol, propanol, butanol, pentanol, hexanol, and a combination thereof, and most preferably the solvent is selected from the group consisting of water, ethanol, and a combination thereof.

Most preferably, the extract used in the Traditional Chinese Medicine composition of the present disclosure is a combination of the water extract and the ethanol extract of each raw materials. Here, the "water extract" means an extract obtained by extracting herbal raw materials by using water (including cold water, warm water or hot water). Here, the "ethanol extract" refers to an extract obtained by extracting herbal raw materials using absolute ethanol or an ethanol solution in water.

Preferably, the extract used in the Traditional Chinese Medicine composition of the present disclosure is dried. Most preferably, the extract used in the Traditional Chinese Medicine composition of the present disclosure is in the form of died powders or granules.

To obtain the Traditional Chinese Medicine composition of the present disclosure comprising extracts, for example, water can be used to extract the herbal raw materials to obtain a water extract; an ethanol solution in water of various concentrations (such as 40-95%) can be used to extract the herbal raw materials to obtain an ethanol extract; or the water extract and the ethanol extract can be combined to give a combination of water extract and ethanol extract. In some preferred embodiments, the Traditional Chinese Medicine composition of the present disclosure comprises a combination of a water extract and an ethanol extract.

Those skilled in the art can determine the steps and the sequence of the steps used for such extraction as desired, for example, each herbal raw material can be extracted separately and then the extracts are combined; alternatively, some or all of the herbal raw materials are combined and then extracted. The steps and the sequence of the steps used for the extraction may affect extraction efficiency and process efficiency. A relatively more fast and effective extraction method comprises the following steps: the herbal raw materials to be extracted are divided into two groups, A and B, and one group is extracted by water to obtain a water extract, and the extract residues of said one group are combined with the other group and extracted by alcohol (or an alcohol water solution) to obtain an alcohol extract; and the water extract and the alcohol extract are combined. Alternatively, the herbal raw materials to be extracted are divided into two groups, A and B, and one group is extracted by alcohol (or an alcohol water solution) to obtain an alcohol extract, and the extract residues of said one group are combined with the other group and extracted by water to obtain a water extract; and the water extract and the alcohol extract are combined.

Therefore, in certain particular embodiments, the present disclosure further provides a method for preparing an antiviral Traditional Chinese Medicine composition, comprising:
1) extracting Herba Taraxaci, Radix Stemonae and Radix Cynanchi Atrati and other optional herbal raw materials by alcohol to give an alcohol extract;
2) combining the residues obtained during the preparation of the alcohol extract of step 1) with Radix Puerariae, Rhizoma Atractylodis Macrocephalae, and Pseudobulbus Cremastrae Seu Pleiones, and other optional herbal raw materials, extracting the mixture thus obtained by water, concentrating the extract liquid, causing precipitation in the concentrated extract liquid by adding an alcohol, and collecting the supernatant as a water extract; and
3) combining the alcohol extract obtained in step 1) and the water extract obtained in step 2) to obtain the antiviral Traditional Chinese Medicine composition after optional post processing;
wherein the amount of each of the raw material is as follows: Herba Taraxaci 30-70 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight (the preferred amount of each raw material is as described above).

Preferably, said alcohol used in the above steps is an ethanol solution in water, for example 40-95% ethanol solution in water, or 40-80% ethanol solution in water. In particular embodiments, an ethanol solution in water of 60%, 65%, 70%, 75%, 90% or other concentrations can be used.

The "post processing" in step 3) can be any conventional post processing steps well known in the art, and those skilled in the art can determine suitable post processing steps according to the desired form of the composition. For example, if an intermediate product in the form of a solution is desired, no post processing steps are needed. On the other hand, if a composition in solid form is desired, the post processing steps can comprise concentration and then drying to obtain a composition in solid form. The drying may be carried out by any drying method commonly used in the pharmaceutical field, such as spray drying, microwave drying, vacuum drying, and the like.

The method of the present disclosure can comprise additional steps before, after or during the above-mentioned step 1), step 2) and step 3). For example, for the convenience of the operation, the alcohol extract obtained in the step 1) may be concentrated, and the water extract obtained in step 2) may be concentrated. Sterilization can also be carried out if necessary.

A herbal raw material or component referred to as "optional" in the present disclosure may be included in some embodiments while absent in other embodiments. Similarly, steps or processes referred to "optional" may be included in some embodiments while absent in other embodiments.

The inventor has found that the method comprising the above steps 1) to 3) improves the extraction efficiency and is more cost efficient.

The operation parameters such as the duration of the extraction, the number of times of the extraction, the concentration of the ethanol solution, and the amount of the solvent for each step can be adjusted as desired.

In certain embodiments, the alcohol extract of step 1) is prepared as follows: Herba Taraxaci, Radix Stemonae and Radix Cynanchi Atrati are subjected to reflux extraction for 1-3 times, 1-2 hours each time, with 6-10× ethanol and filtered, the filtrates are combined and concentrated under reduced pressure to give the alcohol extract. For example, 8×40-95% ethanol (for example, 60%, 75% or 90% ethanol solution in water) can be used to extract the mixture for 1.5 h and the obtained mixture is filtered; and then 8×40-95% ethanol (for example, 60%, 75% or 90% ethanol solution in water) can be added to further extract the residue for 1.5 h and the obtained mixture is filtered; and the filtrates obtained in these two extraction processes are combined to give the alcohol extract.

In certain embodiments, the water extract of the step 2) is prepared as follows: the residues obtained during the preparation of the alcohol extract are combined with Radix Puerariae, Rhizoma Atractylodis Macrocephalae, and Pseudobulbus Cremastrae Seu Pleiones, the mixture thus obtained is subjected to reflux extraction for 1-3 times, 1-4 hours each time, with 6-12× water and filtered, the filtrates obtained are concentrated to obtain a thick paste; ethanol solution in water (for example 70-95% ethanol solution in water) is added to the thick paste to achieve a final concentration of 60-80 ethanol % and the precipitate formed is filtered off after setting for 12-48 hours to give the water extract. For example, the residues obtained during the preparation of the alcohol extract are combined with Radix Puerariae, Rhizoma Atractylodis Macrocephalae, and Pseudobulbus Cremastrae Seu Pleiones, the mixture thus obtained is subjected to extraction for 2 hours with 10× water and filtered; then the remaining mixture is again subjected to extraction for 2 hours with 10× water and filtered; the filtrates obtained in these two extraction processes are combined and concentrated to obtain a thick paste; 70 or 95% ethanol solution in water is added to the thick paste to achieve a final concentration of 70 ethanol % and the precipitate is filtered off after setting for 36 hours to give the water extract.

In some embodiments, step 3) comprises combining the alcohol extract obtained in step 1) and the water extract obtained in step 2) and subjecting the combination to concentration and spray drying to obtain the antiviral Traditional Chinese Medicine composition.

The antiviral Traditional Chinese Medicine composition of the present disclosure is prepared from Herba Taraxaci, Radix Stemonae, Pseudobulbus Cremastrae Seu Pleiones, Radix Puerariae, Rhizoma Atractylodis Macrocephalae, and Radix Cynanchi Atrati as raw materials. If desired, the Traditional Chinese Medicine composition of the present disclosure may comprise other herbal raw materials (or herbal extracts).

For example, the inventor has found that the Traditional Chinese Medicine composition of the present disclosure would be more suitable for in vivo application if Cortex Lycii and Cortex Mori are added. For example, the antiviral composition of the present disclosure comprising Cortex Lycii and Cortex Mori as additional raw materials has excellent antipyretic effect, which helps a patient to mount a defense against the viruses, thereby further enhancing the antiviral effect of the Traditional Chinese Medicine composition of the present disclosure.

The term "Cortex Lycii" used herein refers to the dried root bark of *Lycium chinense* Mill. or *Lycium barbarum* L. from the family of Solanaceae.

The term "Cortex Mori" used herein refers to the dried root bark of *Morus alba* L. from the family of Moraceae.

Thus, in certain particular embodiments, the antiviral Traditional Chinese Medicine composition of the present disclosure further comprises Cortex Lycii and Cortex Mori, wherein the amount of Cortex Mori is 20-60 parts by weight (preferably 20-55 parts by weight, more preferably from 20-50 parts by weight, most preferably 25-40 parts by weight), and the amount of Cortex Lycii is 20-60 parts by weight (preferably 20-55 parts by weight, more preferably 20-50 parts by weight, most preferably 30-parts by weight).

Therefore, in certain particular embodiments, the present disclosure provides an antiviral Traditional Chinese Medicine composition comprising an extract of herbal raw materials, which comprise Herba Taraxaci, Radix Stemonae, Pseudobulbus Cremastrae Seu Pleiones, Radix Puerariae, Rhizoma Atractylodis Macrocephalae, Radix Cynanchi Atrati, Cortex Lycii and Cortex Mori, wherein the amount of each raw material is as follows (any one of the preferred ranges of each of the raw materials can be combined with any one of the preferred ranges of other raw materials):
Herba Taraxaci: 30-70 parts by weight, preferably 30-60 parts by weight, more preferably 35-55 parts by weight, most preferably 40-50 parts by weight;
Radix Stemonae: 20-40 parts by weight, preferably 25-35 parts by weight, most preferably 25-30 parts by weight;
Pseudobulbus Cremastrae Seu Pleiones: 20-40 parts by weight, preferably 25-parts by weight, most preferably 25-30 parts by weight;
Radix Cynanchi Atrati: 20-50 parts by weight, preferably 20-45 parts by weight, more preferably 20-40 parts by weight, most preferably 25-35 parts by weight;
Radix Puerariae: 20-50 parts by weight, preferably 20-45 parts by weight, more preferably 20-40 parts by weight, most preferably 25-35 parts by weight;
Rhizoma Atractylodis Macrocephalae: 20-60 parts by weight, preferably 20-55 parts by weight, more preferably 20-50 parts by weight, most preferably 30-40 parts by weight;
Cortex Mori: 20-60 parts by weight, preferably 20-55 parts by weight, more preferably 20-50 parts by weight, most preferably 25-40 parts by weight;
Cortex Lycii: 20-60 parts by weight, preferably 20-55 parts by weight, more preferably 20-50 parts by weight, most preferably 30-40 parts by weight.

In certain particular embodiments, the Traditional Chinese Medicine composition of the present disclosure consists of the extract of Herba Taraxaci, Radix Stemonae, Pseudobulbus Cremastrae Seu Pleiones, Radix Puerariae, Rhizoma Atractylodis Macrocephalae, Radix Cynanchi Atrati, Cortex Lycii and Cortex Mori in the above specified amounts.

In other particular embodiments, other herbal materials may be contained in the Traditional Chinese Medicine composition of the present disclosure as raw material in addition to Herba Taraxaci, Radix Stemonae, Pseudobulbus Cremastrae Seu Pleiones, Radix Puerariae, Rhizoma Atractylodis Macrocephalae, Radix Cynanchi Atrati, Cortex Lycii and Cortex Mori as needed or for other purposes.

Thus, in certain particular embodiments, the present disclosure further provides a method for preparing an antiviral Traditional Chinese Medicine composition, comprising:
1) extracting Herba Taraxaci, Radix Stemonae, Radix Cynanchi Atrati and Cortex Mori by alcohol to give an alcohol extract;
2) combining the residues obtained during the preparation of the alcohol extract of step 1) with Radix Puerariae, Rhizoma Atractylodis Macrocephalae, Pseudobulbus Cremastrae Seu Pleiones, and Cortex Lycii, extracting the mixture thus obtained by water, concentrating the extract liquid, causing precipitation in the concentrated extract liquid by adding an alcohol, and collecting the supernatant as a water extract; and
3) combining the alcohol extract obtained in step 1) and the water extract obtained in step 2) to obtain the antiviral Traditional Chinese Medicine composition after optional post processing;
wherein the amount of each of the raw material is as follows: Herba Taraxaci 30-70 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, Rhizoma Atractylodis Macrocephalae 20-60 parts by weight, Cortex Mori 20-60 parts by weight, and Cortex Lycii 20-60 parts by weights (the preferred amount of each raw material is as described above).

Preferably, said alcohol used in the above steps is an ethanol solution in water, for example 40-95% ethanol solution in water, or 40-80% ethanol solution in water. In particular embodiments, an ethanol solution in water of 60%, 65%, 70%, 75%, 90% or other concentrations can be used. The "post processing" in step 3) can be determined by a skilled artisan according to the desired form of the end product.

The Traditional Chinese Medicine composition of the present disclosure, as an active pharmaceutical ingredient, can be formulated into formulations according to conventional techniques in pharmaceutical engineering using pharmaceutically acceptable carrier or adjuvant. The active pharmaceutical ingredient in the formulation may be from 0.1 to 99.9% (e.g., 1-99% or 50-98% or 50-95%, etc.), with the balance being a pharmaceutically acceptable carrier or adjuvant.

The formulation of the present disclosure can be in any pharmaceutically acceptable dosage form, including: granules, tablets, sugar-coated tablets, film-coated tablets, enteric coated tablets, capsules, oral liquids, dripping pills, dissolving granules, pills, pulvis, suspensions, powders or the like.

Preferably, the formulation of the present disclosure is an oral dosage form such as granules, tablets, capsules, pills or the like.

Preferably, the formulation of the present disclosure is in the form of a unit dosage form, in which a single unit of the formulation is for example a tablet, a pouch of granules, or a capsule.

The unit dosage form preferably comprises about 1% to about 90% (e.g., 20-80% or 30-60%) active pharmaceutical ingredient. For example, the unit dosage form for a single administration, such as a capsule, a tablet or a sugar-coated pill, may contain about 1 mg to about 100 g (e.g. 10 mg to 80 g, 50 mg to 50 g, 1 g to 20 g, etc.) active pharmaceutical ingredient.

To prepare a suitable dosage form, the Traditional Chinese Medicine composition of the present disclosure, as the active pharmaceutical ingredient, may be optionally mixed or combined with an inorganic or organic, solid or liquid pharmaceutically acceptable carrier or adjuvant suitable for administration. For example, suitable carriers include, in particular, fillers such as sugars (for example lactose), mannitol or sorbitol, cellulose preparations and/or calcium phosphate (tricalcium phosphate or calcium hydrogen phosphate); binders such as starch paste, gelatin, methyl cellulose and/or polyvinyl vinylpyrrolidone; disintegrants such as starch, carboxymethyl starch, crosslinked polyvinylpyrrolidone, agar, or alginic acid or a salt thereof (for example, sodium alginate).

In certain particular embodiments, the present disclosure further provides a method of treating a viral infectious disease or condition in a patient in need thereof, the method comprises administering to the patient an effective amount of the Traditional Chinese Medicine composition according to any one of the embodiments of the present invention. The patient is preferably a mammal, and more preferably a human being. The administration is preferably oral administration.

In certain particular embodiments, the present disclosure also provides use of the Traditional Chinese Medicine composition according to any one of the embodiments of the present invention for treating a disease or condition caused by a virus in a patient. The patient is preferably a mammal, and more preferably a human.

In certain particular embodiments, the present disclosure also provides use of a Traditional Chinese Medicine composition according to any one of the embodiments of the present invention for the manufacture of a medicament for the treatment of a viral infectious disease or condition. The disease or condition is preferably a disease or condition in a mammal, especially a human. The medicament is preferably in oral form.

In certain particular embodiments, the present disclosure also provides a Traditional Chinese Medicine composition according to any one of the embodiments of the invention for use in the treatment of a viral infectious disease or condition. The disease or condition is preferably a disease or condition in a mammal, especially a human. The Traditional Chinese Medicine composition is preferably in oral form.

The terms "treat", "treating" and "treatment" used herein are to be construed to refer to prophylactic or preventive treatment, as well as curative or palliative treatment of a viral infectious disease or condition.

The terms "viral infectious disease or condition" and "a disease or condition caused by a virus" have the same meaning and are used interchangeably herein to refer to a disease or condition caused by the transmission and infection of a virus.

The virus infectious disease or condition particularly suitable for treatment with the Traditional Chinese Medicine composition of the present disclosure is a disease or condition caused by a virus from the families of Orthomyxoviridae, Flaviviridae or Togaviridae, in particular virus from Flavivirus genus of Flaviviridae, Alphavirus genus of Togaviridae, or Influenza A virus genus of Orthomyxoviridae, such as influenza, eastern equine encephalitis (EEE), western equine encephalitis (WEE), Venezuelan equine encephalitis (VEE), Japanese encephalitis (JE), Russian spring summer encephalitis (RSSE), hepatitis C (HCV), dengue fever, etc. Most preferably, the Traditional Chinese Medicine composition of the present disclosure is particularly suitable for the treatment or prevention of diseases caused by influenza A virus (including H1N1, H7N7 and H9N2 viruses, etc.), Zika virus, dengue virus (including dengue type I and dengue type II virus), or chikungunya virus, comprising: flu, chikungunya fever, dengue fever (DF), dengue hemorrhagic fever (DHF), dengue shock syndrome (DSS), Zika virus disease, microcephaly disease, etc.

The mode of administration and the dosage of the treatment can be determined by a physician according to the specifics of the patient, especially the age, body weight, lifestyle, activity level, severity of disease, etc.

In general, a single dose for a mammal is in the range of about 1-20,000 mg/kg. For example, for the preferred subject, i.e. a human being, a suitable dose may be in the range of 1-2,000 mg/kg, 2-1,000 mg/kg, 5-500 mg/kg or 10-100 mg/kg when administered as a herbal extract premix. If desired, such doses can be divided (optionally evenly) into several portions. The above mentioned doses may be administered at regular intervals, for example, three times a day, once a day, once a week, and the like.

The term "mg/kg" or "$mg \cdot kg^{-1}$" used in the present specification means milligrams per kilogram of the body weight of the mammal (including human) to be treated, and "g/kg" or "$g \cdot kg^{-1}$" means grams per kilogram of the body weight of the mammal (including human) to be treated.

The preferred values and aspects in various embodiments and features of the present invention mentioned above can be combined arbitrarily, and various embodiments obtained by such combination are within the scope of the claims.

Some beneficial effects of the present invention are described as follows.

The Traditional Chinese Medicine composition of the present disclosure has activity against a variety of acute infectious viruses and has a good safety profile. In vitro and in vivo pharmacodynamics tests show that the Traditional Chinese Medicine composition of the present disclosure has significant broad-spectrum antiviral activity, especially against Influenza H1N1, H7N7 and H9N2 virus, Zika virus, dengue I type and dengue II type virus, and chikungunya virus; the present composition may also improve immunity, and may be efficient as an adjuvant therapy; toxicology tests show that the composition has good safety: the no observed adverse effect level (NOAEL) in monkey after 1 month of administration is equivalent to about 15 times of the clinical dose.

The Traditional Chinese Medicine composition of the present disclosure has the potential to become a broad-spectrum herbal oral drug against various infectious viruses, which can be used for prevention and treatment of various viral infections, and can solve drug resistance problems caused by frequent mutation of the viruses. Also, it is safe and easy to use, and thus will be a revolutionary breakthrough in clinical treatment in related field.

BRIEF DESCRIPTION OF THE DRAWINGS

FIG. 1 is a graphical representation showing the results of experiments in which the traditional Chinese medicinal composition of Example 1 prevents the replication of dengue type II virus in Vero cells. The y-axis marked as "Den 2 E1/1000 β-actin" shows the copy of the dengue type II virus in Vero cells, which is calculated as the copy number of the E1 gene in dengue type II virus per 1000 β-actin proteins; while for the x-axis, "Mock" represents virus control group (cell+culture); "0" represents virus control group (cell+virus+culture), and "Drug" represents the tested drug. "" means p<0.01; "*" means p<0.001.

FIG. 2 is a plot showing the cytotoxicity of the traditional Chinese medicinal composition of Example 1 in Vero cells tested by the LDH method. The "% Cytotoxicity" in the y-axis means the percentage of cytotoxicity, the "Lysis Buffer" in the x-axis represents cell lysate, "cells only" means that only cells are present, and "Drug" represents the drug tested.

FIG. 3 is a graphical representation showing the results of experiments in which the traditional Chinese medicinal composition of Example 2 prevents the binding of Zika virus to Vero cells. The y-axis marked as "ZIKV E1/β-actin" shows the binding of Zika virus to Vero cells, which is calculated as the copy number of the E1 gene in Zika virus per a β-actin protein; while for the x-axis, "Mock" represents virus control group (cell+culture); "0" represents virus control group (cell+virus+culture), and "Drug" represents the tested drug. "*" means p<0.05.

FIG. 4 is a plot showing the results of plaque forming assay testing the inhibitory effect of the traditional Chinese medicinal composition of Example 4 against chikungunya virus. The y-axis marked as "Number The plaque" shows the number of the plaque, the y-axis marked as "Plaque neutralization (%)" represents the plaque neutralization percentage, while the "Drug" in the x-axis represents the drug tested.

FIG. 5 is a graphical representation showing the results of in vitro experiments in which the traditional Chinese medicinal composition of Example 5 prevents the binding of chikungunya virus to cellular receptors. The y-axis marked as "CHIKV E1/β-actin" shows the binding of chikungunya virus to Vero cells, which is calculated as the copy number of the E1 gene in chikungunya virus per a β-actin protein; while for the x-axis, "Mock" represents virus control group (cell+culture); "0" represents virus control group (cell+virus+culture), and "Drug" represents the tested drug. "*" means p<0.05.

FIG. 6 is a plot showing the results of plaque forming assay testing the inhibitory effect of the traditional Chinese medicinal composition of Example 6 against Zika virus. The y-axis marked as "Plaque neutralization (%)" represents the plaque neutralization percentage, while the "Drug" in the x-axis represents the drug tested.

FIG. 7 is a graphical representation showing the results of experiments in which the traditional Chinese medicinal composition of Example 6 reduces the level of Zika virus in blood. The y-axis marked as "ZIKV E1/100 β-actin" shows the copy of the Zika virus in blood of mice, which is calculated as the copy number of the E1 gene in Zika virus per 100 β-actin proteins; while for the x-axis, "Control" represents control group, "Medium" represents the drug group with medium dose, "High" represents the drug group with high dose; "d2" means day 2, and "d4" means day 4.

FIG. 8 is a graphical representation showing the results of experiments in which the traditional Chinese medicinal composition of Example 6 inhibits the replication of Zika virus in spleen, brain and uterus. The y-axis marked as "ZIKV E1/100 β-actin" shows the copy of the Zika virus in blood of mice, which is calculated as the copy number of the E1 gene in Zika virus per 100 β-actin proteins; while for the x-axis, "Control" represents control group, "Medium" represents the drug group with medium dose, "High" represents the drug group with high dose; "Spleen" means spleen, "Brain" means brain, and "Uterus" means uterus.

FIG. 9 is a graphical representation showing the effect of the traditional Chinese herbal composition of Example 6 on the body weight of mice. The y-axis marked by "wt in grams" shows the body weight of the mouse (in gram); while for the x-axis, "Before" means before administration, "after" means after administration; "Control" represents control group, "Medium" represents the drug group with medium dose, and "High" represents the drug group with high dose.

EXAMPLES

Figure 1:
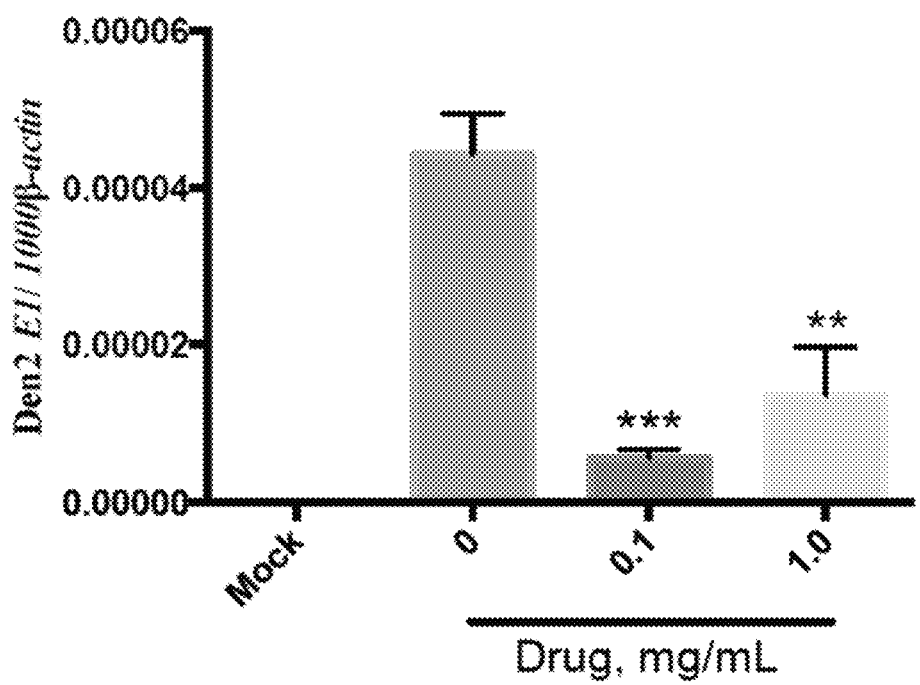

The embodiments of the present invention will be further described in detail below by way of exemplary Examples. It is understood that the Examples described herein are merely illustrative and are not intended to limit the scope of the claims. Any modification made within the spirit and principal of the present invention, and any improvement made or equivalents obtained according to common technical knowledge and conventional means in the art should be included in the scope of the claims.

The numbers reported in the following Examples are as accurate as possible, but those skilled in the art will understand that each number should be understood as an approximate value rather than an absolutely accurate number due to unavoidable measurement errors and variation in operational parameters. For example, due to an error caused by weighing apparatus, the weight values for each materials in each composition in the Examples should be understood as having a ±2% or ±1% error.

Example 1

The formulation of the Traditional Chinese Medicine composition of Example 1 was as follows:
Herba Taraxaci: 470 g
Radix Stemonae: 280 g
Pseudobulbus Cremastrae Seu Pleiones: 280 g
Radix Cynanchi Atrati: 315 g
Radix Puerariae: 315 g
Rhizoma Atractylodis Macrocephalae: 380 g Herba Taraxaci was collected from Hebei, China; Radix Cynanchi Atrati was collected from Henan, China, Radix Puerariae was collected from Hebei, China, Radix Stemonae was collected from Guangxi, China, Pseudobulbus Cremastrae Seu Pleiones was collected from Sichuan, China, and Rhizoma Atractylodis Macrocephalae was collected from Zhejiang, China.

The process for preparing the Traditional Chinese Medicine composition of Example 1 was as follows:
(1) 470 g Herba Taraxaci, 280 g Radix Stemonae and 315 g Radix Cynanchi Atrati were subjected to extraction with 8×60% ethanol for 1.5 h and the obtained mixture was filtered; and then 8×60% ethanol was added to extract for another 1.5 h, the obtained mixture was filtered; and the filtrates obtained in these two extraction processes were combined to give an alcohol extract;

(2) the residues obtained during the preparation of the alcohol extract were combined with 315 g Radix Puerariae, 280 g Pseudobulbus Cremastrae Seu Pleiones and 380 g Rhizoma Atractylodis Macrocephalae, the mixture thus obtained was subjected to extraction for 2 hours with 10× water and filtered; then the remaining mixture was again subjected to extraction for 2 hours with 10× water and filtered, the filtrates obtained in these two extraction processes were combined and concentrated to obtain a thick paste; 90% ethanol was added to the thick paste and stirred to achieve a final concentration of about 75 ethanol % and a water extract was obtained by taking the supernatant after a 24 hours settling; and (3) the alcohol extract obtained in step 1) and the water extract obtained in step 2) were combined, concentrated and spray dried to give the Traditional Chinese Medicine composition of Example 1. The resulting composition was a brown powder, the weight of which was about 0.34 kg, and it was used directly in the following in vivo and in vitro experiments.

In the following the Traditional Chinese Medicine composition of Example 1 (referred to as "tested drug" or "tested substance") was studied in various pharmacodynamics experiments to verify its efficacy.

1. In Vitro Experiment Using the Composition of Example 1 Testing its Inhibition of Dengue Type II Virus (Dengue-2) Calculated by Copy Number Vero cells (African green monkey kidney cells, available from the American Type Culture Collection (ATCC), CCL-81) were plated in a 6-well plate at $6\times10^5$/well and incubated under 5% $CO_2$ at 37° C. for 24 hours and monolayer was formed. The tested substance was dissolved in PBS buffer, filter sterilized, and diluted to 1.0 mg/ml and 0.1 mg/ml. The dengue type II virus (obtained from the American Type Culture Collection ATCC, VR-1584) and 0.1 mg/ml or 1.0 mg/ml tested substance were added to Vero monolayer, and incubated at 37° C. for 24 hours. Quantitative analysis of intracellular viral replication (dengue type II E gene) was conducted by qPCR, see Paul A M, Shi Y, Acharya D, et al. *Delivery of Antiviral Small Interfering RNA with Gold Nanoparticles Inhibits Dengue Virus Infection in vitro.* [J]. *Journal of General Virology,* 2014, 95(8):1712-22 for details.

The results of the PCR experiment showed that the tested substance can significantly inhibit the replication of the dengue type II virus in vitro (see FIG. 1).

2. Lactate Dehydrogenase (LDH) Assay Testing the Cytotoxicity of the Composition of Example 1 in Vero Cells The LDH Cytotoxicity Detection Kit$^{PLUS}$ kit (purchased from Roche Diagnostics) was used for this test. The protocol is described in the instructions in the kit. The procedure is briefly described as follows: 100 μl Vero cells (obtained from the American Type Culture Collection (ATCC), CCL-81) was plated in 96-well cell culture plate at $4\times10^4$/well and two replicate wells were included (i.e., duplicates for each experiment). The plates were incubated overnight under 5% $CO_2$ at 37° C. The tested substance was dissolved in PBS buffer, sterilized by filtration, and diluted to 1.0, 0.25, 0.125, 0.0625, 0.03125, and 0.0156 mg/ml, respectively. 10 μL tested substances of various concentrations (2.0, 1.0, 0.25, 0.125, 0.0625, 0.03125, 0.0156 mg/ml) were added to the cell culture plate, and 10 μL PBS was used as a blank control (two duplicate wells were included). The plates were incubated for 24 hours and 48 hours under 5% $CO_2$ at 37° C. After incubation, the LDH concentration in the medium was measured by ELx808 Ultramicroplate Reader (Bio Tek) at 450 nm, and cytotoxicity was calculated according to the instructions in the kit.

Figure 2:
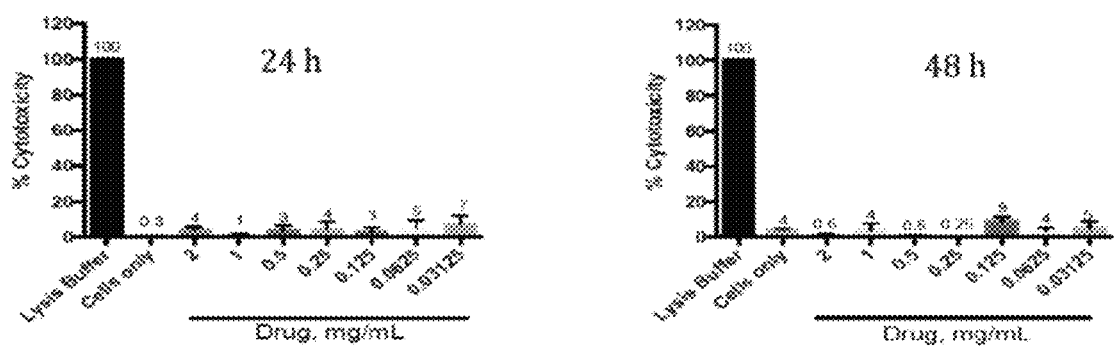

The results showed that no evident cytotoxicity was observed in Vero cells after incubation for 48 hours with 2 mg/ml tested substance (see FIG. 2). These results rule out the possibility that the inhibition of dengue virus by the tested substance is due to cytotoxicity, and further confirm that the tested substance can inhibit dengue virus infection in vitro.

Example 2

The formulation of the Traditional Chinese Medicine composition of Example 2 was as follows:
Herba Taraxaci: 680 g
Radix Stemonae: 390 g
Pseudobulbus Cremastrae Seu Pleiones: 400 g
Radix Cynanchi Atrati: 480 g
Radix Puerariae: 440 g
Rhizoma Atractylodis Macrocephalae: 540 g The origins of the above herbal raw materials are the same as the origins described in Example 1. The process for preparing the Traditional Chinese Medicine composition of Example 2 was as follows:

(1) 680 g Herba Taraxaci, 390 g Radix Stemonae and 480 g Radix Cynanchi Atrati were subjected to extraction with 10×60% ethanol for 1.5 h and the obtained mixture was filtered; and then 10×60% ethanol was added to extract for another 1.5 h, the obtained mixture was filtered; and the filtrates obtained in these two extraction processes were combined to give an alcohol extract;

(2) the residues obtained during the preparation of the alcohol extract were combined with 440 g Radix Puerariae, 400 g Pseudobulbus Cremastrae Seu Pleiones and 540 g Rhizoma Atractylodis Macrocephalae, the mixture thus obtained was subjected to extraction for 2 hours with 8× water; after filtration the remaining mixture was again subjected to extraction for 2 hours with 8× water and filtered, the filtrates obtained in these two extraction processes were combined and concentrated to obtain a thick paste; 90% ethanol was added to the thick paste and stirred to achieve a final concentration of about 75 ethanol % and the water extract was obtained by taking the supernatant after a 24 hours settling; and (3) the alcohol extract obtained in step 1) and the water extract obtained in step 2) were combined, concentrated and spray dried to give the Traditional Chinese Medicine composition of Example 2. The resulting composition was a brown powder, the weight of which was about 0.5 kg, and it was used directly in the following in vivo and in vitro experiments.

Then, the Traditional Chinese Medicine composition of Example 2 (referred to as "tested drug" or "tested substance") was studied in various pharmacodynamics experiments to verify its efficacy.

1. In Vitro Pharmacodynamics Study Testing the Inhibition of Zika Virus (ZIKV) by the Composition of Example 2

The origin and the handling of the Vero cells are the same as described in Example 1. Vero cells were plated in a 6-well plate at $6\times10^5$/well and incubated under 5% $CO_2$ at 37° C. for 24 hours and monolayer was formed. The Zika virus (provided by CDC Arbovirus Branch) at 1 MOI and 0.1 mg/ml or 1.0 mg/ml tested substance solution in water were combined and added to the Vero monolayer, and incubated at 4° C. for 1 hour. At this temperature, the virus is able to bind to the receptors on cell surface but cannot enter into cytoplasm. After the incubation, the cells were washed with culture medium at 4° C. to remove the unbound virus. The cells were collected and total RNA was extracted using Trizol, single-strand cDNA was synthesized. Quantitative analysis of coat protein gene and house-keeping gene β-actin was conducted by real-time qPCR, see Acharya D, Bastola P, Le L, et al. *An Ultrasensitive Electrogenerated Chemiluminescence-based Immunoassay for Specific Detection of Zika Virus* [*J*]. *Scientific Reports*, 2016, 6:32227 for details.

Figure 3:
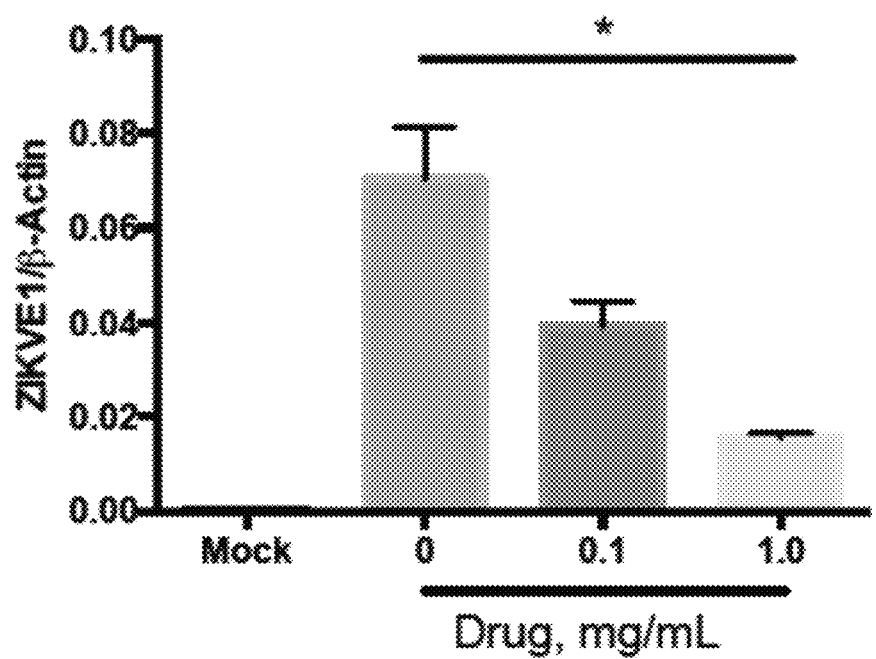

The results showed that the tested substance at 0.1 mg/ml or 1.0 mg/ml can inhibit the binding of about 40% or about 80% Zika virus respectively to the receptors (see FIG. 3).

Example 3

The formulation of the Traditional Chinese Medicine composition of Example 3 was as follows:
Herba Taraxaci: 310 g
Radix Stemonae: 200 g
Pseudobulbus Cremastrae Seu Pleiones: 190 g
Radix Cynanchi Atrati: 210 g
Radix Puerariae: 210 g
Rhizoma Atractylodis Macrocephalae: 250 g The origins of the above herbal raw materials are the same as the origins described in Example 1. The process for preparing the Traditional Chinese Medicine composition of Example 3 was as follows:
(1) 310 g Herba Taraxaci, 200 g Radix Stemonae and 210 g Radix Cynanchi Atrati were subjected to extraction with 10×60% ethanol for 1.5 h and the obtained mixture was filtered; and then 10×60% ethanol was added to extract for another 1.5 h, the obtained mixture was filtered; and the filtrates obtained in these two extraction processes were combined to give an alcohol extract;
(2) the residues obtained during the preparation of the alcohol extract were combined with 210 g Radix Puerariae, 190 g Pseudobulbus Cremastrae Seu Pleiones and 250 g Rhizoma Atractylodis Macrocephalae, the mixture thus obtained was subjected to extraction for 2 hours with 8× water; after filtration the remaining mixture was again subjected to extraction for 2 hours with 8× water and filtered, the filtrates obtained in these two extraction processes were combined and concentrated to obtain a thick paste; 90% ethanol was added to the thick paste and stirred to achieve a final concentration of about 80 ethanol % and the water extract was obtained by taking the supernatant after a 24 hours settling; and
(3) the alcohol extract obtained in step 1) and the water extract obtained in step 2) were combined, concentrated and spray dried to give the Traditional Chinese Medicine composition of Example 3. The resulting composition was a brown powder, the weight of which was about 0.23 kg, and it was used directly in the following in vivo and in vitro experiments.

In the following the Traditional Chinese Medicine composition of Example 3 (referred to as "tested drug" or "tested substance") was studied in various pharmacodynamics experiments to verify its efficacy.

1. In Vitro Pharmacodynamics Study Testing the Inhibition of Influenza H7N7 Virus by the Composition of Example 3
1) Determination of Toxicity Concentration 50% ($TCID_{50}$) of Virus on MDCK Cells by CPE Method 100 μL MDCK cells (canine kidney epithelial cells, provided by the Office of High-tech Research on Animal Biological Formulations, Institute of Animal Husbandry and Veterinary, Beijing Academy of Agriculture and Forestry) were seeded in the wells of a 96-well plate at $2\times10^4$ cells/well, and incubated at 37° C. for 24 h, and monolayer was formed. An avian influenza virus H7N7 strain (provided by Institute of Animal Husbandry and Veterinary, Beijing Academy of Agriculture and Forestry) was diluted to from $10^{-3}$ to $10^{-12}$ by 10× serial dilution (totally 10 concentrations) and added to the wells (8 wells for each concentration) and incubated at 37° C. The cells were monitored daily using an inverted microscope for cytopathic effect (CPE). The level of cytopathic effect (CPE) was recorded. The toxicity concentration 50% ($TCID_{50}$) of virus was calculated by Reed-Muench method.

After being infected with virus, the cells appeared to be swollen, netting, shrinking, and aggregated. The $TCID_{50}$ of avian influenza virus H7N7 was determined to be $10^{-4.19}$/0.1 ml.

2) Determination of the Inactivation of Avian Influenza Virus H7N7 by the Tested Substance
100 μL MDCK cells were seeded in the wells of a 96-well plate at $2\times10^4$ cells/well, and incubated under 5% $CO_2$ at 37° C. for 24 h, and monolayer was formed. The supernatant was discarded, solutions of the tested substance at various concentrations were mixed with an equal volume of $100TCID_{50}$ influenza virus in the test tube and allowed to react for 6 hours, and then the mixture was seeded to the plate. The experiment included normal cell control group, positive control drug group (amantadine hydrochloride, available from Sigma) and virus control group. After absorption for 2 h, the supernatant was discarded, and a cell maintenance medium was added, and incubation was continued at 37° C., under 5% $CO_2$ in an incubator. The cytopathic effect was recorded and the cell viability was determined by MTT staining. The experiment was repeated 2 times. The data were subjected to Probit regression analysis using the statistical software SPSS13.0 to calculate inhibitory concentration 50% ($IC_{50}$).

The results are shown in Table 3-1, wherein inhibitory concentration 50% ($IC_{50}$) of the tested drug was measured to be 410 μg/mL and 447 μg/mL, demonstrating that the tested substance is capable of inactivating avian influenza virus H7N7.

TABLE 3-1 inhibitory activity of the tested substance on H7N7 virus ($\bar{x} \pm SD$)

| Group | Concentration (μg/ml) | OD value (A) | | Inhibition (/%) | IC50 (μg/ml) |
|---|---|---|---|---|---|
| Tested substance | 1250 | 1.24 ± 0.15 | 1.18 ± 0.14 | 88 83 | 410 447 |
| | 625 | 0.85 ± 0.11 | 0.82 ± 0.08 | 59 56 | |
| | 312.5 | 0.66 ± 0.16 | 0.62 ± 0.06 | 45 42 | |
| | 156.25 | 0.57 ± 0.04 | 0.49 ± 0.13 | 38 31 | |
| | 78.12 | 0.30 ± 0.06 | 0.23 ± 0.01 | 18 12 | |
| | 39.06 | 0.24 ± 0.03 | 0.20 ± 0.01 | 13 9 | |

TABLE 3-1-continued inhibitory activity of the tested substance on H7N7 virus (x̄ ± SD)

| Group | Concentration (μg/ml) | OD value (A) | | Inhibition (/%) | IC50 (μg/ml) |
|---|---|---|---|---|---|
| Adamantanamine | 312.5 | 1.15 ± 0.09 | 1.09 ± 0.10 | 81 76 | 62 66 |
| | 156.25 | 1.01 ± 0.07 | 0.98 ± 0.09 | 71 68 | |
| | 78.12 | 0.86 ± 0.08 | 0.81 ± 0.04 | 60 55 | |
| | 39.06 | 0.55 ± 0.04 | 0.57 ± 0.07 | 36 38 | |

Example 4

The formulation of the Traditional Chinese Medicine composition of Example 4 was as follows:
Herba Taraxaci: 560 g
Radix Stemonae: 320 g
Pseudobulbus Cremastrae Seu Pleiones: 350 g
Radix Cynanchi Atrati: 360 g
Radix Puerariae: 380 g
Rhizoma Atractylodis Macrocephalae: 460 g The origins of the above herbal raw materials are the same as the origins described in Example 1. The process for preparing the Traditional Chinese Medicine composition of Example 4 was as follows:
(1) 560 g Herba Taraxaci, 320 g Radix Stemonae and 360 g Radix Cynanchi Atrati were subjected to extraction with 10×60% ethanol for 1.5 h and the obtained mixture was filtered; and then 10×60% ethanol was added to extract for another 1.5 h, the obtained mixture was filtered; and the filtrates obtained in these two extraction processes were combined to give an alcohol extract;
(2) the residues obtained during the preparation of the alcohol extract were combined with 380 g Radix Puerariae, 350 g Pseudobulbus Cremastrae Seu Pleiones and 460 g Rhizoma Atractylodis Macrocephalae, the mixture thus obtained was subjected to extraction for 2 hours with 8× water; after filtration the remaining mixture was again subjected to extraction for 2 hours with 8× water and filtered, the filtrates obtained in these two extraction processes were combined and concentrated to obtain a thick paste; 90% ethanol was added to the thick paste and stirred to achieve a final concentration of about 80 ethanol % and the water extract was obtained by taking the supernatant after a 24 hours settling; and
(3) the alcohol extract obtained in step 1) and the water extract obtained in step 2) were combined, concentrated and spray dried to give the Traditional Chinese Medicine composition of Example 4. The resulting composition was a brown powder, the weight of which was about 0.4 kg, and it was used directly in the following in vivo and in vitro experiments.

In the following the Traditional Chinese Medicine composition of Example 4 (referred to as "tested drug" or "tested substance") was studied in various pharmacodynamics experiments to verify its efficacy.
1. In Vitro Pharmacodynamics Study Testing the Inhibition of Chikungunya Virus (CHIKV) by the Composition of Example 4

The origin and the handling of the Vero cells are the same as described in Example 1. Chikungunya virus was provided by the Connecticut Agricultural Test Station. Chikungunya virus (about 150 PFU) was incubated for 1 hour at room temperature with freshly prepared aqueous solutions of tested substance of 2.0, 1.0, 0.5, 0.25, and 0.125 mg/ml, respectively, after which the solutions were added to Vero monolayer and incubated at 37° C. for 1 hour and then the formation of plaques was evaluated. For details, see Acharya D, Paul A M, Anderson J F, et al. Loss of Glycosaminoglycan Receptor Binding after Mosquito Cell Passage Reduces Chikungunya Virus Infectivity. [J]. Plos Neglected Tropical Diseases, 2015, 9(10):e0004139.

Figure 4:
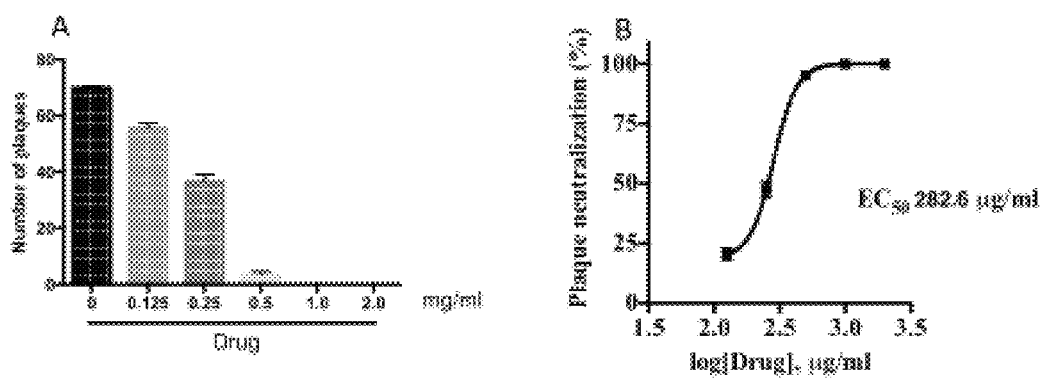

The results in the plaque neutralization test showed that the tested substance can suppress Chikungunya virus in a dose-dependent manner, and the $EC_{50}$ value was 282.6 μg/ml (FIG. 4).

Example 5

The formulation of the Traditional Chinese Medicine composition of Example 5 was as follows:
Herba Taraxaci: 370 g
Radix Stemonae: 220 g
Pseudobulbus Cremastrae Seu Pleiones: 230 g
Radix Cynanchi Atrati: 270 g
Radix Puerariae: 270 g
Rhizoma Atractylodis Macrocephalae: 280 g The origins of the above herbal raw materials are the same as the origins described in Example 1. The process for preparing the Traditional Chinese Medicine composition of Example 5 was as follows:
(1) 370 g Herba Taraxaci, 220 g Radix Stemonae and 270 g Radix Cynanchi Atrati were subjected to extraction with 10×60% ethanol for 1.5 h and the obtained mixture was filtered; and then 10×60% ethanol was added to extract for another 1.5 h, the obtained mixture was filtered; and the filtrates obtained in these two extraction processes were combined to give an alcohol extract;
(2) the residue obtained during the preparation of the alcohol extract were combined with 270 g Radix Puerariae, 230 g Pseudobulbus Cremastrae Seu Pleiones and 280 g Rhizoma Atractylodis Macrocephalae, the mixture thus obtained was subjected to extraction for 2 hours with 8× water; after filtration the remaining mixture was again subjected to extraction for 2 hours with 8× water and filtered, the filtrates obtained in these two extraction processes were combined and concentrated to obtain a thick paste; 90% ethanol was added to the thick paste and stirred to achieve a final concentration of about 80 ethanol % and the water extract was obtained by taking the supernatant after a 24 hours settling; and
(3) the alcohol extract obtained in step 1) and the water extract obtained in step 2) were combined, concentrated and spray dried to give the Traditional Chinese Medicine composition of Example 5. The resulting composition was a brown powder, the weight of which was about 0.28 kg, it was used directly in the following in vivo and in vitro experiments.

In the following the Traditional Chinese Medicine composition of Example 5 (referred to as "tested drug" or "tested substance") was studied in various pharmacodynamics experiments to verify its efficacy.

1. In Vitro Pharmacodynamics Study Testing the Inhibition of Chikungunya Virus (CHIKV) by the Composition of Example 5

The origin and the handling of the Vero cells are the same as described in Example 1. The origin of the chikungunya virus is the same as described in Example 4. Vero cells were plated in a 6-well plate at $6\times10^5$/well and incubated under 5% $CO_2$ at 37° C. for 24 hours and monolayer was formed. The chikungunya virus and 0.1 mg/ml or 1.0 mg/ml tested substance solution in water were combined and added to the monolayer, and incubated at 4° C. for 1 hour. At this temperature, the virus is able to bind to the receptors on cell surface but cannot enter into cytoplasm. After the incubation, the cells were washed with culture medium at 4° C. to remove the unbound virus. The cells were collected and total RNA were extracted using Trizol, single-strand cDNA was synthesized. Quantitative analysis of coat protein gene and house-keeping gene β-actin of chikungunya virus was conducted by real-time qPCR, see Acharya D, Paul A M, Anderson J F, et al. *Loss of Glycosaminoglycan Receptor Binding after Mosquito Cell Passage Reduces Chikungunya Virus Infectivity.* [J]. *Plos Neglected Tropical Diseases*, 2015, 9(10):e0004139 for details.

Figure 5:
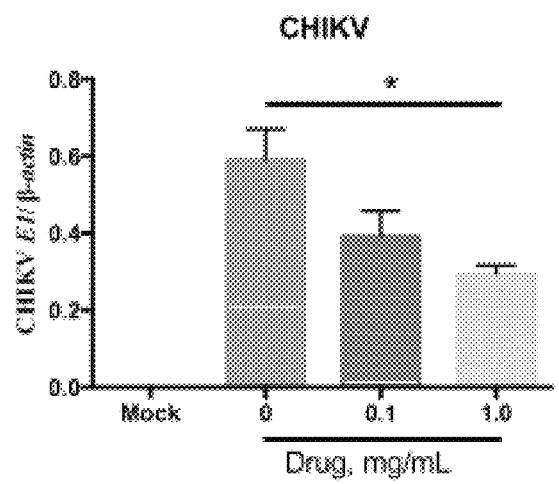

The results show that the tested substance at 0.1 mg/ml or 1.0 mg/ml can inhibit some of the bindings of CHIKV virus to the receptors on Vero cells (see FIG. 5).

Example 6

The formulation of the Traditional Chinese Medicine composition of Example 6 was as follows:
Herba Taraxaci: 480 g
Radix Stemonae: 290 g
Pseudobulbus Cremastrae Seu Pleiones: 290 g
Radix Cynanchi Atrati: 320 g
Radix Puerariae: 320 g
Rhizoma Atractylodis Macrocephalae: 385 g
Cortex Mori: 320 g
Cortex Lycii: 385 g Herba Taraxaci was collected from Hebei, China; Radix Cynanchi Atrati was collected from Henan, China; Radix Puerariae was collected from Hebei, China; Radix Stemonae was collected from Guangxi, China; Pseudobulbus Cremastrae Seu Pleiones was collected from Sichuan, China; Rhizoma Atractylodis Macrocephalae was collected from Zhejiang, China; Cortex Mori was collected from Shandong, China; and Cortex Lycii was collected from Ningxia autonomous region, China.

The process for preparing the Traditional Chinese Medicine composition of Example 6 was as follows:

(1) 480 g Herba Taraxaci, 290 g Radix Stemonae, 320 g Radix Cynanchi Atrati and 320 g Cortex Mori were subjected to extraction with 8×60% ethanol for 1.5 h and the obtained mixture was filtered; and then 8×60% ethanol was added to extract for another 1.5 h, the obtained mixture was filtered; and the filtrates obtained in these two extraction processes were combined to give an alcohol extract;

(2) the residue obtained during the preparation of the alcohol extract were combined with 320 g Radix Puerariae, 290 g Pseudobulbus Cremastrae Seu Pleiones 385 g Rhizoma Atractylodis Macrocephalae and 385 g Cortex Lycii, the mixture thus obtained was subjected to extraction for 2 hours with 10× water; after filtration the remaining mixture was again subjected to extraction for 2 hours with 10× water and filtered, the filtrates obtained in these two extraction processes were combined and concentrated to obtain a thick paste; 90% ethanol was added to the thick paste and stirred to achieve a final concentration of about 70 ethanol % and the water extract was obtained by taking the supernatant after a 36 hours settling; and (3) the alcohol extract obtained in step 1) and the water extract obtained in step 2) were combined, concentrated and spray dried to give the Traditional Chinese Medicine composition of Example 6. The resulting composition was a brown powder, the weight of which was about 0.48 kg, it was used directly in the following in vivo and in vitro experiments.

In the following the Traditional Chinese Medicine composition of Example 6 (referred to as "tested drug" or "tested substance") was studied in various pharmacodynamics experiments to verify its efficacy.

1. In Vitro Pharmacodynamics Study Testing the Inhibition of Influenza H9N2 Virus by the Composition of Example 6

1.1 Determination of Toxicity Concentration 50% ($TCID_{50}$) of Virus on MDCK Cells by CPE Method 100 µL MDCK cells (canine kidney epithelial cells, provided by Institute of Animal Husbandry and Veterinary, Beijing Academy of Agriculture and Forestry) were seeded in the wells of a 96-well plate at $2\times10^4$ cells/well, and incubated at 37° C. for 24 h, and monolayer was formed. Avian influenza virus H9N2 (provided by Beijing Academy of Agriculture and Forestry) was diluted to from $10^{-3}$ to $10^{-12}$ by 10× serial dilution (totally 10 concentrations) and added to the wells (8 wells for each concentration) and incubated at 37° C. The cells were monitored daily using an inverted microscope for cytopathic effect (CPE). The infection dose 50% ($TCID_{50}$) of virus was calculated by Reed-Muench method.

After infected with virus, the cells appeared to be swollen, netting, shrinking, and aggregated. The $TCID_{50}$ of avian influenza virus H9N2 was determined to be $10^{-3.5}$/0.1 ml.

1.2 Determination of Inhibitory Concentration 50% ($TC_{50}$) of MDCK Cells by the Tested Substance Using MTT Method 100 µL MDCK cells were seeded in the wells of a 96-well plate at $2\times10^4$ cells/well, and incubated under 5% $CO_2$ at 37° C. for 24 h, and monolayer was formed. The supernatant was discarded, solutions of the tested substance at 10000, 5000, 2500, 1250, 625, 312.5, 156.25, 78.12, and 39.06 µg/mL in water were added (4 wells per each concentration) and a cell control group was included (cell+culture medium). Amantadine (available from Sigma) was used as the positive control drug and its concentration was 312.5, 156.25, 78.12, and 39.06 µg/mL (4 wells per each concentration). After 3 days of observation, MTT was added to stain the cells for 4 hours, the supernatant was discarded and DMSO was added to dissolve for 0.5 hours, and OD 570 nm value was determined by Microplate Reader (see Table 6-1). The data were subjected to Probit regression analysis using the statistical software SPSS13.0 to calculate inhibitory concentration 50% ($IC_{50}$) for the drugs.

$$\text{Survival rate } (\%) = \frac{\text{Average } OD \text{ value of the test group}}{\text{Average } OD \text{ value of the cell control group}} \times 100\%$$

Upon the Probit regression analysis of the data by SPSS13.0, inhibitory concentration 50% ($TC_{50}$) of the tested drug on MDCK cells was determined to be 1596 µg/mL. The maximum non-toxic concentration of the tested drug on MDCK cells was determined to be 1250 µg/mL, at which the cell morphology was the same as the control cells. In contrast, the maximum non-toxic concentration of amantadine was 312.5 μg/mL.

TABLE 6-1 toxicity of the tested substance on MDCK cells ($\bar{x} \pm SD$)

| Group | Concentration (μg/ml) | OD value (A) | Survival rate (/%) |
|---|---|---|---|
| tested substance | 10000 | 0.24 ± 0.03 | 20 |
| | 5000 | 0.139 ± 0.01 | 12 |
| | 2500 | 0.197 ± 0.03 | 17 |
| | 1250 | 0.89 ± 0.02 | 75 |
| | 625 | 0.93 ± 0.11 | 79 |
| | 312.5 | 0.94 ± 0.01 | 80 |
| | 156.25 | 1.11 ± 0.14 | 95 |
| | 78.12 | 1.18 ± 0.11 | 100 |
| | 39.06 | 1.18 ± 0.14 | 100 |
| amantadine | 312.5 | 0.97 ± 0.03 | 82 |
| | 156.25 | 0.96 ± 0.05 | 81 |
| | 78.12 | 1.05 ± 0.02 | 89 |
| | 39.06 | 1.20 ± 0.04 | 100 |
| blank | 0 | 1.18 ± 0.16 | 100 |

1.3 Determination of the Inactivation of Avian Influenza Virus H9N2 by the Tested Substance 100 μL MDCK cells were seeded in the wells of a 96-well plate at 2×10$^4$ cells/well, and incubated under 5% CO$_2$ at 37° C. for 24 h, and monolayer was formed. The supernatant was discarded, solutions of the tested substance at various concentrations were mixed with an equal volume of 100TCID$_{50}$ influenza virus in the test tube and allowed to react for 6 hours, and then the mixture was seeded to the plate. The experiment included a normal cell control group, positive control drug group (amantadine, available from Sigma) and virus control group. After absorption for 2 h, the supernatant was discarded, and a cell maintenance medium was added, and incubation was continued at 37° C., under 5% CO$_2$ in an incubator. The cytopathic effect was recorded and the cell viability was determined by MTT staining. The experiment was repeated 2 times. The data were subjected to Probit regression analysis using the statistical software SPSS13.0 to calculate inhibitory concentration 50% (IC$_{50}$).

The results are shown in Table 6-2, wherein the inhibitory concentration 50% (IC$_{50}$) of the tested drug was measured to be 380.5 μg/mL, demonstrating that the tested substance is capable of inactivating avian influenza virus H9N2.

TABLE 6-2 inhibitory activity of the tested substance of H9N2 virus ($\bar{x} \pm SD$)

| Group | Concentration (μg/ml) | OD value (A) | | Inhibition (/%) | | IC50 (μg/ml) | |
|---|---|---|---|---|---|---|---|
| tested substance | 1250 | 0.75 ± 0.03 | 0.76 ± 0.03 | 77 | 76 | 385 | 376 |
| | 625 | 0.66 ± 0.02 | 0.69 ± 0.02 | 66 | 68 | | |
| | 312.5 | 0.54 ± 0.02 | 0.58 ± 0.02 | 53 | 55 | | |
| | 156.25 | 0.43 ± 0.04 | 0.43 ± 0.04 | 41 | 42 | | |
| | 78.12 | 0.38 ± 0.03 | 0.42 ± 0.06 | 34 | 38 | | |
| | 39.06 | 0.29 ± 0.02 | 0.32 ± 0.06 | 24 | 27 | | |
| amantadine | 312.5 | 0.83 ± 0.02 | 0.84 ± 0.16 | 86 | 83 | 63 | 66 |
| | 156.25 | 0.71 ± 0.07 | 0.68 ± 0.15 | 72 | 66 | | |
| | 78.12 | 0.64 ± 0.05 | 0.46 ± 0.03 | 65 | 42 | | |
| | 39.06 | 0.37 ± 0.02 | 0.32 ± 0.03 | 34 | 27 | | |

2. In Vitro Pharmacodynamics Study Testing the Inhibition of Zika Virus (ZIKV) by the Composition of Example 6

Vero cells (African green monkey kidney cells, obtained from the American Type Culture Collection (ATCC), CCL-81) were plated at 6×10$^5$/well in a 6-well plate and incubated at 5% CO$_2$ and 37° C. for 24 hours and monolayer was formed; the tested substance was dissolved in PBS buffer and filter sterilized, and diluted to 1.0, 0.25, 0.125, 0.0625, 0.03125, and 0.0156 mg/ml, respectively. Zika virus (provided by CDC Arbovirus Branch) and the tested substance diluted with DMEM cell culture medium (1% L-glutamine, 1% penicillin/streptomycin and 10% FBS) to different concentrations were mixed and incubated for 1 hour at room temperature. Then, the mixture was added to wells containing Vero monolayer cells, and incubated at 37° C. and 5% CO$_2$ for 1 hour to allow the virus to permeate into the cells or be taken up by the cells. After the virus were removed, the cells were plated on a 1% agarose gel and incubated at 37° C. and 5% CO$_2$ for 4 days. After staining with 0.3% neutral red, the plate was taken out and the staining medium was removed; the plate was put back into the incubator for 1-2 h, and then the uncolored plaque on red background was clearly observed on a white backboard. The average number of plaques for each concentration was counted.

Figure 6:
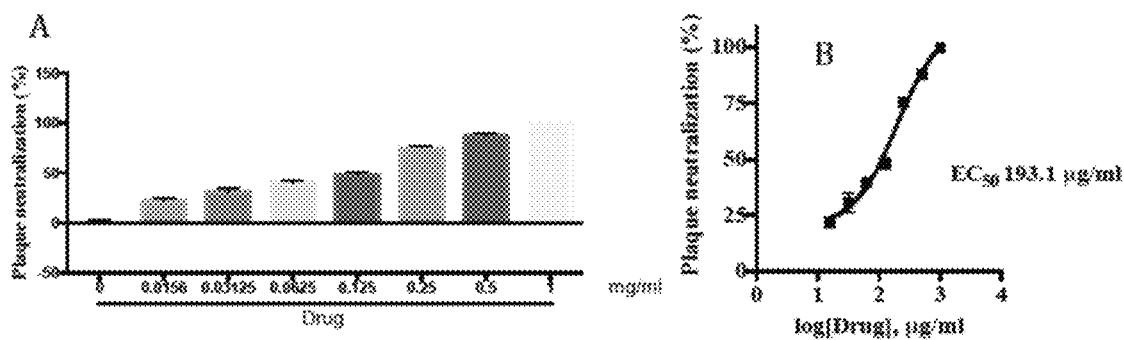

This In vitro experiment showed that the tested substance is able to inhibit Zika virus effectively, and the half effective dose of the tested substance to inhibit the formation of Zika virus plaque was determined to be 193.1 μg/ml (see FIG. 6).

3. In Vivo Pharmacodynamics Study Testing Zika Virus (ZIKV) Infection of Female Mice by the Composition of Example 6

To study the inhibitory effect of the tested substance on Zika virus infection in mice, C57BL/6 female mice (5 weeks old, obtained from The Jackson Laboratory (Bar Harbor, Me.)) were weighed on the first day of the experiment and each mouse was intraperitoneally injected with 2 mg IFNR1 antibody (MAR1-5A3). On day 2, each mouse was infected by intraperitoneally injecting 1×10$^4$ PFU Zika virus (provided by the CDC Arbovirus Branch) and the mice were divided into three groups (10 per group): placebo group (Control), medium dose group (Medium) and the high dose group (High). 4 hour after infection, the placebo group was administered via oral gavage 100 μl sterile water, the medium dose group was administered via oral gavage 100 μl water solution of tested substance at a dose of 0.75 g/kg, the high dose group was administered via oral gavage 100 μl water solution of tested substance at a dose of 1.50 g/kg, and the administrations were conducted once per day for 6 days.

Figure 7:
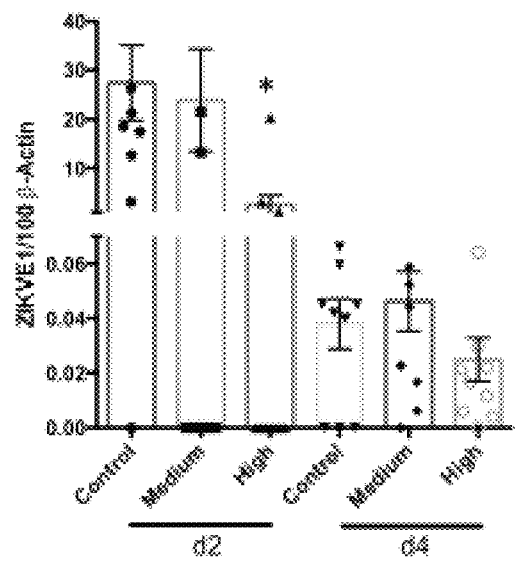

On day 2 and day 4 after Zika virus infection, orbital bloods were collected from mice for RNA extraction, cDNA synthesis and mRNA qPCR analysis of Zika virus and mouse β-actin (the method is the same as in Example 2). The qPCR results showed that the tested substance significantly inhibited the replication of Zika virus in the bloods of mice at high dose on day 2 after infection (p<0.05), and showed a tendency of inhibition on day 4 after infection (see FIG. 7).

Figure 8:
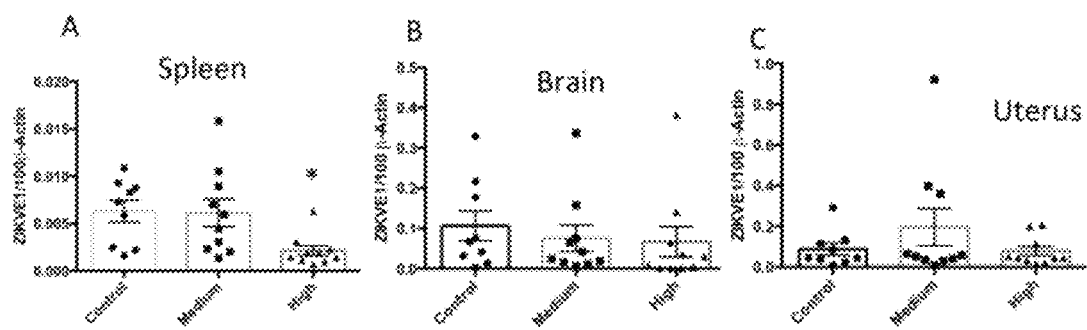

The morbidity and mortality of the mice were observed daily. All the animals appeared normal expect for one animal in the placebo group, which died between day 3 an day 4. On day 6 after Zika virus infection, all mice were weighed and sacrificed. The spleen, brain and uterus of each mouse were taken, and total RNA in spleen, brain and uterus was extracted, followed by cDNA synthesis and mRNA qPCR analysis of Zika virus and mouse β-actin (the method is the same as described in Example 2). The results showed (see FIG. 8) that tested substance at high dose (1.5 g/kg) can significantly inhibit the infection of Zika virus in the spleen; and the infection of Zika virus in brain and uterus had the tendency to be inhibited although not significant (it is believed that this is likely caused by experimental outliers).

Figure 9:
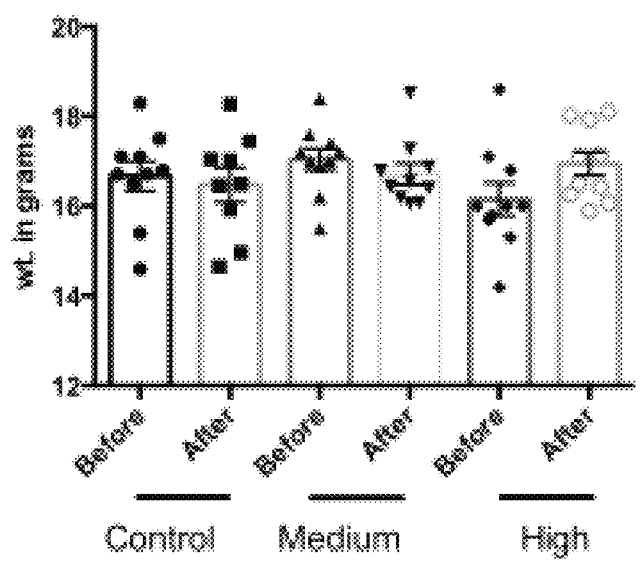

To evaluate the potential toxic effects of the tested substance on mice, the body weights before and after the experimentation were compared and the results showed that the tested substance had no significant effect on body weight, indicating that the tested substance had no side effects on mice (see FIG. 9).

4. Study on the Antipyretic Effect of the Composition of Example 6 Via Oral Administration on Rats 4.1 Test Animals SD rats (Srrague Dawley Rats) were purchased from Chengdu Dashuo Experimental Animal Co., Ltd with a license number of SCXK (Chuan) 2013-24 and a certificate number of 0018409. 15 females and 15 male rats were used in the experiment. The body weights at the time of purchase were 150-170 g, the ages were 8-9 weeks, and the body weights during the experiment were 180-200 g.

Inclusion Criteria:

1) Body weight: animals weighed in the range of 0.18-0.20 kg were selected.

2) The rectal temperatures of the animals were measured once per day at the same time point for three days before the start of the experiment, and animals having rectal temperature of 37.5-38.5° C. with changes no more than 0.5° C. were selected as the rats used for the model.

4.2 Test Design and Periods

Figure 10:
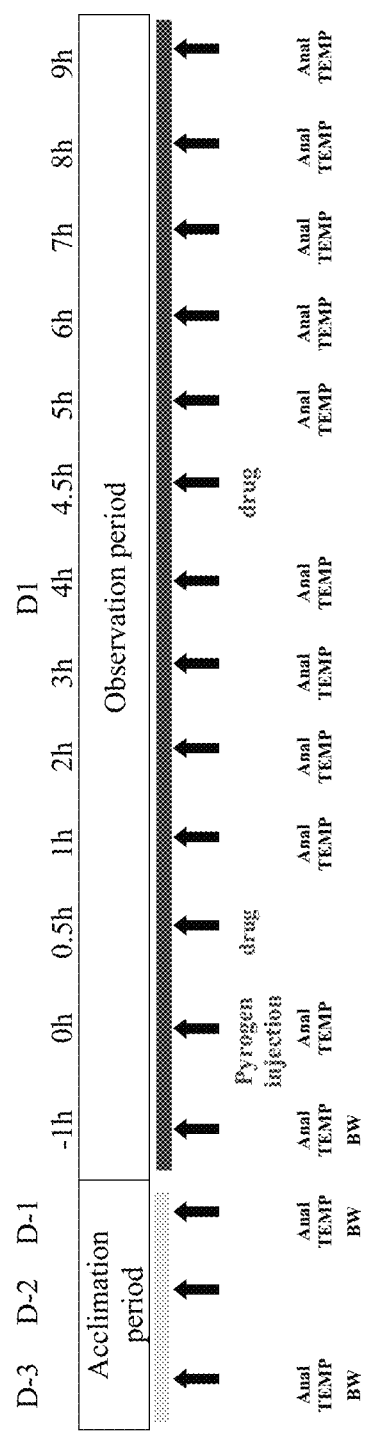
FIG. 10 is a graph showing the schedule of an experiment illustrating the antipyretic effects of the Traditional Chinese Medicine composition of Example 6 in an animal model of fever. The "BW" means body weight and "Anal TEMP" means rectal temperature.

The acclimation period was 3 days, and the observation period after administration was 1 day; the day of administration was indicated by D1. See FIG. 10 for detailed schedule.

4.3 Experiment

In this experiment, SD rats were injected subcutaneously with 20% dry yeast suspension (5 ml·kg$^{-1}$) as a heat source to establish fever model for drug efficacy evaluation. 30 healthy SD rats were selected and randomly divided into 6 groups: tested substance 4 g·kg$^{-1}$ group, tested substance 2 g·kg$^{-1}$ group, tested substance 1 g·kg$^{-1}$ group, positive control aspirin 100 mg·kg$^{-1}$ group, fever model group, and blank control group (5 animals per group). Aspirin was from BAYER corp. 0.5 h and 4.5 h after the injection of pyrogen, administration was done by gavage (totally 2 times). Rectal temperatures were measured 1 h before and 1, 2, 3, 4, 5, 6, 7, 8, 9 hours after the injection of pyrogen (measurement was done by holding the animal tight while it is awake and taking rectal temperature by inserting an OMRON electronic thermometer MC-347 coated with paraffin into the rectum about 4 cm), changes of rectal temperature were recorded and animals were observed for symptoms and signs.

Data processing: the rectal temperature measured 1 h before the injection of pyrogen was used as the baseline value and paired T test was used to analyze changes of the rectal temperature before and after the administration in the animals in each group, and one-way analysis of variance was used to statistically analyze each drug group and the fever model group, wherein P<0.05 indicates statistical significant difference.

4.4 Results and Analysis

During the experiment period, no drug related abnormalities were observed in animals in each group in terms of feces, behavior, activity, and body color.

Rectal temperatures of the rats are shown in Table 6-3 and summarized below.

Blank control group: body temperature at each time point fluctuated within the normal range.

Fever model group (5 rats): compared to the baseline values, the body temperatures of the rats at 1-4 hours after injection of pyrogen maintained within the normal range, the rectal temperature started to show a significant tendency of increasing 5 hours after the infection (P<0.01), and significant increase was observed at 6, 7, 8, and 9 hours (P<0.01). Therefore, changes of rectal temperature at 5, 6, 7, 8 and 9 hours after injection of the pyrogen were analyzed as the efficacy endpoint.

Aspirin 100 mg·kg$^{-1}$ group (5 rats, equivalent to 2-4× clinical dose, which is 0.3 g-0.6 g/human/time): compared to the baseline values, the rectal temperatures of the rats at 5-8 hours (4 time points) after injection of pyrogen maintained within the normal range, body temperatures started to show a significant tendency of increasing 9 hours after the infection (P<0.05); compared to the fever model group, rectal temperatures were significantly decreased at 5, 6, 7, and 8 hours after the injection of pyrogen (P<0.01), the rectal temperatures of the rats began to increase at 9 hours. The above results indicate that aspirin 100 mg·kg$^{-1}$ can maintain the effect of reducing the body temperature for 4 hours starting from 4.5 h after the injection of the pyrogen.

Tested substance 4 g·kg$^{-1}$ group (5 rats): compared to the baseline values, the rectal temperatures of the rats at 5-9 hours (5 time points) after injection of pyrogen maintained within the normal range; compared to the fever model group, rectal temperatures were significantly decreased at 5, 6, 7, 8 and 9 hours after the injection of pyrogen (P<0.01). The above results indicate that the antipyretic effect reduced the body temperature rapidly at 4.5 h after the injection of the pyrogen and the effect was maintained for 5 hours. The antipyretic effect was comparable to that of the aspirin 100 mg·kg$^{-1}$ and lasted longer than aspirin 100 mg·kg$^{-1}$ group (by 1 hour).

Tested substance 2 g·kg$^{-1}$ group (5 rats): compared to the baseline values, the body temperatures at 5 hours after the injection of pyrogen were the same as baseline, but increased significantly or very significantly at 6, 7, 8 and 9 hours (P<0.05 or P<0.01); compared to the fever model group, the body temperature has the tendency of decreasing at 5, 6, 8 and 9 hours after the injection of pyrogen, and significantly decreased at 7 hours (P<0.01).

Tested substance 1 g·kg$^{-1}$ group: compared to the baseline value, the body temperatures at 5, 6, 7, 8, and 9 hours after the injection of pyrogen were significantly or very significantly increased (P<0.05 or P<0.01); compared to the fever model group, rectal temperatures of the animals were comparable at 5, 6, 7, 8, and 9 hours after the injection of pyrogen.

TABLE 6-3

Effect of the tested substance on the rectal temperature in dry yeast induced fever in rats (° C.)

| group | Baseline-value$^a$ | After the injection of pyrogen | | | | | | | | |
|---|---|---|---|---|---|---|---|---|---|---|
| | | 1 h | 2 h | 3 h | 4 h | 5 h | 6 h | 7 h | 8 h | 9 h |
| Blank control group (n = 5) | 37.6 ± 0.3 | 37.4 ± 0.3 | 37.3 ± 0.4 | 37.9 ± 0.4 | 37.6 ± 0.3 | 37.4 ± 0.2 | 37.5 ± 0.3 | 37.4 ± 0.3 | 37.4 ± 0.3 | 37.7 ± 0.2 |

TABLE 6-3-continued

Effect of the tested substance on the rectal temperature in dry yeast induced fever in rats (° C.)

| | | time | | | | | | | | |
|---|---|---|---|---|---|---|---|---|---|---|
| | Baseline- | After the injection of pyrogen | | | | | | | | |
| group | value$^a$ | 1 h | 2 h | 3 h | 4 h | 5 h | 6 h | 7 h | 8 h | 9 h |
| Fever model group (n = 5) | 37.7 ± 0.5 | 37.6 ± 0.3 | 37.4 ± 0.3 | 37.7 ± 0.3 | 37.9 ± 0.4 | 38.4 ± 0.5** | 39.1 ± 0.5*** | 39.5 ± 0.3*** | 39.5 ± 0.3*** | 39.2 ± 0.3*** |
| Aspirin 100 mg/kg group (n = 5) | 37.8 ± 0.4 | 38.0 ± 0.3 | 37.5 ± 0.2 | 37.7 ± 0.3 | 37.8 ± 0.2 | 38.1 ± 0.6 | 38.1 ± 0.4$^\#$ | 38.3 ± 0.5$^{\#\#}$ | 38.5 ± 0.5$^{\#\#}$ | 38.8 ± 0.4* |
| Tested substance 4 g/kg group (n = 5) | 37.9 ± 0.5 | 37.9 ± 0.6 | 37.5 ± 0.4 | 37.7 ± 0.4 | 37.9 ± 0.3 | 37.4 ± 0.5$^{\#\#}$ | 37.3 ± 1.3$^{\#\#\#}$ | 38.0 ± 1.2$^{\#\#\#}$ | 38.4 ± 0.9$^{\#\#\#}$ | 38.1 ± 0.9$^{\#\#}$ |
| Tested substance 2 g/kg group (n = 5) | 37.8 ± 0.2 | 37.4 ± 0.2 | 37.6 ± 0.2 | 37.8 ± 0.3 | 38.0 ± 0.2 | 38.0 ± 0.5 | 38.9 ± 0.3*** | 38.9 ± 0.3***$^{\#\#}$ | 39.2 ± 0.4*** | 39.1 ± 0.4*** |
| Tested substance 1 g/kg group (n = 5) | 37.9 ± 0.5 | 37.7 ± 0.3 | 37.7 ± 0.2 | 38.0 ± 0.4 | 38.1 ± 0.3 | 38.7 ± 0.3* | 38.8 ± 0.2* | 39.3 ± 0.3* | 39.5 ± 0.3** | 39.0 ± 0.5** |

Notes:
1. $^\#$p < 0.05, $^{\#\#}$p < 0.01, $^{\#\#\#}$p < 0.001 each drug group vs. fever model group.
2. *p < 0.05, p < 0.01, *p < 0.001 each drug group vs. baseline value.
3. $^a$indicates the rectal temperature of the animal measured 1 h before the injection of pyrogen.

4.5 Conclusions

Aspirin 100 mg·kg$^{-1}$ group (equivalent to 2-4× clinical dose, which is 0.3 g-0.6 g/human/time) significantly reduced the body temperature (5-8 hours after injection of pyrogen), and the effect was maintained for 4 hours.

Tested substance 4 g·kg$^{-1}$ significantly reduced the body temperature (5-9 hours after the injection of the pyrogen), indicating that the antipyretic effect is comparable to that seen in aspirin 100 mg·kg$^{-1}$ group, and the therapeutic effect is fast and maintained for 5 hours, which outlasted aspirin 100 mg·kg$^{-1}$ by one hour. Tested substance 2 g·kg$^{-1}$ significantly reduced the body temperature, and the efficacy and duration of the therapeutic effect were reduced compared to aspirin 100 mg·kg$^{-1}$. In conclusion, the antipyretic effect of the tested substance is clearly dose-related and is considered to be related to administration.

On one hand, the antipyretic effect of the Traditional Chinese Medicine composition of the present disclosure helps to enhance the resistibility of the patient to the virus, thereby further enhancing the antiviral efficacy of the Traditional Chinese Medicine composition of the present disclosure. On the other hand, since viral infection is usually accompanied by fever, the antipyretic effect of the Traditional Chinese Medicine composition of the present disclosure shows its efficacy not only in terms of antiviral ability but also in the significant amelioration of the clinical symptoms in patients infected by the virus.

5. Toxicity Test of the Composition of Example 6 in Healthy Rhesus Monkeys by Repeated Oral Administration for 30 Days 5.1 Test Animals Variety: rhesus monkey Level: Normal level, tested to be qualified before the experimentation, including physical examination, *Mycobacterium tuberculosis*, parasite, *Salmonella*, *Shigella* and B virus tests.

Number and Sex: 3 male, 5 female

Weight: 2.2-3.5 kg

Identification: stainless steel number plate on the neck ring and cage card.

Supplier: Ya'an Primed Biotechnology Co., Ltd., Sichuan, China

License number: SCXK (Chuan) 2014-27

Certificate number: 0016929

5.2 Test Method 5.2.1 Test Design and Periods

Figure 11:
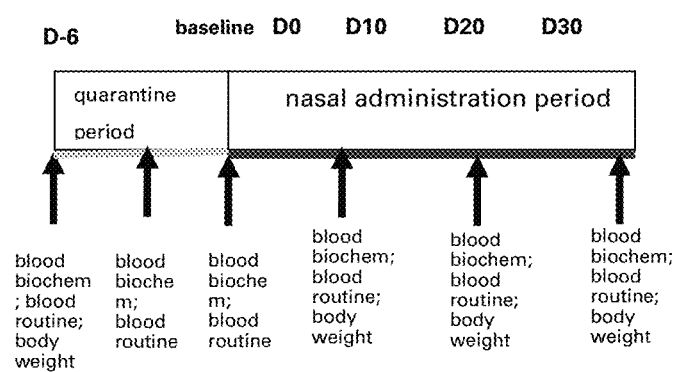
FIG. 11 is a graph showing the schedule of an experiment testing the toxicity of the Traditional Chinese Medicine composition of Example 6 in rhesus.

The quarantine period was 39 days, and nasal feeding was for 30 days, the day of the first administration was indicated as D0. See FIG. 11 for test design.

5.2.2 Animal Grouping and Dose Design Grouping criteria: body weight.

Grouping method: stratified randomization.

Group design: tested substance group and placebo group, total two groups, 3 animals in the test group and 5 animals in the placebo group.

Dose of the tested substance: 15× clinical equivalent dose for monkeys, which is also 18× pharmacodynamic equivalent dose (mouse 0.75 mg/kg) for monkeys.

Based on the effective dose for mice, a dose equivalent to 15× human dose was used for the toxicity test, which was 3375 mg/kg (see the table below).

TABLE 6-4

| Group design | | | |
|---|---|---|---|
| Group | Group code | Dosage (mg/kg) | Number of the animal |
| Tested substance group | A | 3375 | 3 |
| Placebo group | C | 0 | 5 |

5.2.3 Administration

Route of administration: nasal feeding for 30 days.

Frequency of administration: once per day for 30 days.

Calculation of the dose: the dose for a 10-day period was calculated according to the body weight measured during the previous 10-day period.

Time of administration: around 08:00-09:00 AM every day, delayed for 30 min if a blood sampling was scheduled.

5.2.4 Tests 5.2.4.1 Observation of Clinical Symptoms

Frequency: once per day.

Method: observing before the cage

Objects: skin, back hair, eyes, ear, nose, mouth cavity, chest, abdomen, genitourinary organs, limbs, etc., as well as breathing, exercise, urinary, defecation and behavioral changes.

5.2.4.2 Determination of Food Intake

Period: from quarantine period to the end of the administration.

Feeding schedule: fed once at 7:45~8:30 AM and 2:00~3:00 PM respectively; for the first week during the drug administration period, 150 g in the morning and 100 g in the afternoon; for the second week during the drug administration period, 200 g in the morning and 150 g in the afternoon; the remaining feed was removed at 7:40~8:00 the next morning.

Dosage: 200 g-400 g/animal/day. Reason: the average daily feed intake for rhesus monkeys is about 200 g-400 g/animal/day. The feed during this test was gradually increased: for the first week, 150 g in the morning and 100 g in the afternoon; for the second week, 200 g in the morning and 150 g in the afternoon, ad libitum.

Method of measuring food intake: record the amount of food given, the amount of discarded food and the remaining amount of the food in the food container. Food intake=food given—discarded food—remaining food in the food container. The amount percentage of the feed was determined semi-quantitatively as 0%, 25%, 50%, 75% and 100%, and the daily food intake was calculated as the amount of the daily feed multiplied by the amount percentage.

5.2.4.3 Weight Measuring

Time: before feeding.

Frequency: 2 times during quarantine period (before grouping), and once every 10 days, a total of 5 times.

Method: animals were taken out by skilled workers while they were awake, and weighed on a large animal scale (TCS-150).

5.2.4.4 Biochemical Test of Blood

Frequency: 2 times before administration period, once every 10 days during the administration period, 5 times in total.

Sampling method: the animals were fasted overnight before blood collection, and the blood collection was done at 08:00-08:30 the next day with no anesthesia. 1.0 ml blood was taken through the forearm vein; after the collection, sterile dry cotton ball was used to gently press the blood collection site. Coagulation promoting tube was used for the collection, serum was separated at 5000 rpm for 10 min at 4° C. for use in the biochemical tests. Markers tested: total cholesterol (CHO), aspartate aminotransferase (AST), alanine aminotransferase (ALT), ALT/AST, glucose (GLU), total bilirubin (TBIL), direct bilirubin (DBIL), indirect bilirubin (IBIL), total protein (TP), albumin (ALB), globulin (GLO), ALB/GLO, triglyceride (TG), glutamyltransferase (γ-GGT), high density lipoprotein (HDL-C), and low density lipoprotein (LDL-C) (see Table 6-5 for details). Detection method: all markers were detected by Roche Cobas C501.

TABLE 6-5

Biochemical test of blood

| Marker tested | unit | Test method |
|---|---|---|
| aspartate aminotransferase (AST) | IU/L | colorimetry |
| alanine aminotransferase (ALT) | IU/L | IFCC rate assay |
| total cholesterol (CHO) | mmol/L | Enzyme colorimetry, 1 point endpoint test |
| fructosamine | µmol/L | rate assay |
| glucose (GLU) | mmol/L | hexokinase method, 2 points endpoint test |
| total bilirubin (TBIL) | µmol/L | Diazotization, 2 points endpoint test |
| direct bilirubin (DBIL) | µmol/L | Diazotization, 2 points endpoint test |
| creatine phosphokinase (CK) | g/L | Colorimetry, rate assay |
| urea nitrogen (BUN) | mmol/L | Colorimetry, rate assay |
| creatinine(CR-S) | µmol/L | rate assay |
| uric acid (URIC) | µmol/L | Enzyme colorimetry |
| alkaline phosphatase (ALP) | IU/L | Colorimetry, rate assay |
| total protein(TP) | g/L | Colorimetry, 2 points endpoint test |
| albumin (ALB) | g/L | Colorimetry, 2 points endpoint test |
| Triglyceride (TG) | mmol/L | Enzyme colorimetry |
| γ-glutamyltransferase (GGT) | IU/L | Enzyme colorimetry |
| high density lipoprotein (HDL) | mmol/L | Enzyme colorimetry |
| low density lipoprotein (LDL) | mmol/L | Enzyme colorimetry |

5.2.4.5 Haematological Indexes Test

Frequency: 2 times before administration period, once every 10 days during the administration period, 5 times in total.

Sampling method: the animals were fasted overnight before blood collection, and the blood collection was done at 08:00-08:30 the next day with no anesthesia. 1.0 ml blood was taken through the forearm vein; after the collection, sterile dry cotton ball was used to gently press the blood collection site. Blood samples were treated with anticoagulant EDTAK2 and used for haematological indexes test.

Detection indexes: see Table 6-6. Detection methods: the indexes were tested using ADVIA 2120i.

TABLE 6-6

Haematological indexes test

| Index | Unit | Method |
|---|---|---|
| Red blood cell count (RBC) | $10^{12}$/L | two-dimensional laser |
| White blood cell count (WBC) | $10^9$/L | two-dimensional laser |
| Hemoglobin (Hb) | g/L | cyanomethemoglobin |
| Hematocrit (HCT) | % | two-dimensional laser |
| Mean corpuscular volume (MCV) | fL | two-dimensional laser |
| Mean corpuscular hemoglobin (MCH) | pg | two-dimensional laser |
| Mean corpuscular hemoglobin concentration (MCHC) | g/L | two-dimensional laser |
| Cell hemoglobin concentration mean (CHCM) | g/L | two-dimensional laser |
| Red blood cell volume distribution width (RDW) | % | two-dimensional laser |

TABLE 6-6-continued

| | Haematological indexes test | |
|---|---|---|
| Index | Unit | Method |
| Mean HGB distribution width | g/L | two-dimensional laser |
| Mean RBC hemoglobin concentration | g/L | two-dimensional laser |
| Mean RBC hemoglobin content | Pg | two-dimensional laser |
| Red blood cell CH distribution width | Pg | two-dimensional laser |
| Platelet total number (PLT) | $10^9$/L | two-dimensional laser |
| Plateletcrit (PCT) | % | two-dimensional laser |
| Mean platelet volume (MPV) | fL | two-dimensional laser |
| Platelet volume distribution width (PDW) | fL | two-dimensional laser |
| Neutrophil count (NEUT) | $10^9$/L | peroxidase staining + two-dimensional laser |
| Neutrophil count percentage (NEUT %) | % | peroxidase staining + two-dimensional laser |
| Lymphocyte count* (LYMPH) | $10^9$/L | peroxidase staining + two-dimensional laser |
| Lymphocyte count percentage* (LYMPH) | % | peroxidase staining + two-dimensional laser |
| Number of eosinophils (EOS) | $10^9$/L | peroxidase staining + two-dimensional laser |
| Percentage of eosinophils (EOS %) | % | peroxidase staining + two-dimensional laser |
| Number of basophils (BASO) | $10^9$/L | peroxidase staining + two-dimensional laser |
| Percentage of basophils (BASO %) | % | peroxidase staining + two-dimensional laser |
| Number of monocytes (MONO) | $10^9$/L | peroxidase staining + two-dimensional laser |
| Percentage of monocytes (MONO %) | % | peroxidase staining + two-dimensional laser |
| Large unstained cell ratio | % | peroxidase staining + two-dimensional laser |

5.2.5 Data Processing

The results were presented for each animal. Measurement data such as body weight are expressed as "Mean±SD".

5.3 Results and Analysis 5.3.1 Influence on General Activity and Food Intake

Animals in the placebo group did not show abnormalities after administrations. After the tested substance was administered, no apparent abnormalities were observed in test animals. No abnormalities were observed in terms of activities and water drinking, etc.; no abnormal secretions were seen in mouth, eyes and nose; no abnormalities were found in terms of hair colour and breathing. The animals were in good general condition.

5.3.2 Influence on Weight

See the below table for the influence of tested substance on the weight of rhesus monkeys. After administered for 10 days, a transient weight reduction was observed due to stress response to the nasal administration (3/3), followed by weight increase throughout the administration period. No dosing-related body weight change was observed.

TABLE 6-7

Influence of administrating tested substance for 30 days on body weight (kg, Mean ± SD)

| Group | Animal No. | fe/m | baseline[a] | D −6 | D 10 | D 20 | D 30 |
|---|---|---|---|---|---|---|---|
| GROUP A | 6890 | female | 3.22 | 3.32 | 3.26 | 3.32 | 3.32 |
| tested | 6642 | female | 2.56 | 2.72 | 2.54 | 2.58 | 2.60 |
| substance | 6500 | female | 2.94 | 3.22 | 3.06 | 3.12 | 3.26 |
| (3375 mg/kg) | Mean ± SD | | 2.91 ± 0.33 | 3.09 ± 0.32 | 2.95 ± 0.37 | 3.01 ± 0.38 | 3.06 ± 0.40 |
| n = 3 | | | | | | | |
| GROUP C | 6043 | male | 2.78 | 3.06 | 3.08 | 3.16 | 3.08 |
| placebo | 6343 | male | 2.22 | 2.62 | 2.64 | 2.78 | 2.72 |
| group | 6347 | male | 3.02 | 3.32 | 3.22 | 3.32 | 3.28 |
| n = 5 | 6872 | female | 2.90 | 3.08 | 3.08 | 3.22 | 3.12 |
| | 6880 | female | 2.98 | 2.94 | 3.10 | 3.18 | 3.18 |
| | Mean ± SD | | 2.78 ± 0.33 | 3.00 ± 0.26 | 3.02 ± 0.22** | 3.13 ± 0.21** | 3.08 ± 0.21 |

Notes:

1. [a]34 days before administration (D −34)

5.3.3 Influence on Biochemical Indexes

The influence of the tested substance on biochemical indexes in rhesus are shown in Table 6-8 to Table 6-25. There were no obvious abnormalities in the biochemical indexes of the animals in the placebo group. There were no dosing related abnormalities in the blood biochemical indexes of the animals in the test group.

TABLE 6-8

Influence of administrating tested substance for 30 days on ALT (Mean ± SD)

| Group | Animal No. | fe/m | ALT (IU/L) baseline[a] | D 0 | D 10 | D 20 | D 30 |
|---|---|---|---|---|---|---|---|
| GROUP A | 6890 | female | 39.2 | 26.4 | 33.8 | 34.2 | 24.7 |
| tested | 6642 | female | 20.0 | 24.6 | 24.6 | 25.7 | 23.0 |
| substance | 6500 | female | 40.0 | 25.8 | 24.8 | 27.0 | 22.8 |
| (3375 mg/kg) | Mean ± SD | | 33.1 ± 11.3 | 25.6 ± 0.9 | 27.7 ± 5.3 | 29.0 ± 4.6 | 23.5 ± 1.0 |
| n = 3 | | | | | | | |
| GROUP C | 6043 | male | 41.1 | 23.0 | 22.6 | 22.3 | 24.1 |
| placebo | 6343 | male | 44.5 | 57.1 | 60.4 | 48.1 | 106.6 |
| group | 6347 | male | 24.0 | 10.7 | 10.0 | 10.3 | 14.3 |
| n = 5 | 6872 | female | 34.5 | 23.5 | 22.3 | 20.9 | 20.7 |
| | 6880 | female | 270.9 | 60.2 | 37.1 | 58.7 | 71.8 |
| | Mean ± SD | | 83.0 ± 105.3 | 34.9 ± 22.3 | 30.5 ± 19.3 | 32.1 ± 20.4 | 47.5 ± 40.2 |

Notes:
[a]34 days before administration (D −34);

TABLE 6-9

Influence of administrating tested substance for 30 days on AST (Mean ± SD)

| Group | Animal No. | fe/m | AST (IU/L) baseline[a] | D0 | D10 | D20 | D30 |
|---|---|---|---|---|---|---|---|
| GROUP A | 6890 | female | 47.9 | 28.2 | 27.1 | 27.2 | 20.2 |
| tested | 6642 | female | 38.6 | 33.9 | 35.1 | 33.5 | 31.3 |
| substance | 6500 | female | 39.3 | 24.7 | 25.5 | 26.9 | 22.5 |
| (3375 mg/kg) | Mean ± SD | | 41.9 ± 5.2 | 28.9 ± 4.6 | 29.2 ± 5.1 | 29.2 ± 3.7 | 24.7 ± 5.9 |
| n = 3 | | | | | | | |
| GROUP C | 6043 | male | 59.0 | 32.4 | 38.4 | 29.7 | 32.9 |
| placebo | 6343 | male | 41.6 | 30.8 | 36.9 | 34.4 | 44.4 |
| group | 6347 | male | 52.2 | 31.3 | 40.1 | 35.1 | 30.8 |
| n = 5 | 6872 | female | 43.8 | 30.3 | 30.4 | 25.9 | 24.1 |
| | 6880 | female | 105.4 | 41.4 | 36.9 | 35.4 | 37.5 |
| | Mean ± SD | | 60.4 ± 26.1 | 33.2 ± 4.6 | 36.5 ± 3.7 | 32.1 ± 4.2 | 33.9 ± 7.6 |

Notes:
[a]34 days before administration (D-34);

TABLE 6-10

Influence of administrating tested substance for 30 days on ALP (Mean ± SD)

| Group | Animal No. | fe/m | ALP (IU/L) baseline[a] | D0 | D10 | D20 | D30 |
|---|---|---|---|---|---|---|---|
| GROUP A | 6890 | female | 519 | 508 | 430 | 463 | 477 |
| tested | 6642 | female | 585 | 724 | 530 | 506 | 525 |
| substance | 6500 | female | 420 | 594 | 506 | 512 | 418 |
| (3375 mg/kg) | Mean ± SD | | 508 ± 83 | 609 ± 109 | 489 ± 52 | 494 ± 27 | 473 ± 54 |
| n = 3 | | | | | | | |
| GROUP C | 6043 | male | 383 | 479 | 445 | 453 | 445 |
| placebo | 6343 | male | 437 | 478 | 512 | 456 | 473 |
| group | 6347 | male | 317 | 460 | 426 | 422 | 378 |
| n = 5 | 6872 | female | 532 | 640 | 625 | 544 | 487 |
| | 6880 | female | 573 | 528 | 713 | 652 | 732 |
| | Mean ± SD | | 448 ± 105 | 517 ± 73 | 544 ± 122 | 505 ± 94 | 503 ± 135 |

Notes:
[a]34 days before administration (D-34);

TABLE 6-11

Influence of administrating tested substance for 30 days on GGT
(Mean ± SD)

| Group | Animal No. | fe/m | GGT (IU/L) baseline[a] | D0 | D10 | D20 | D30 |
|---|---|---|---|---|---|---|---|
| GROUP A | 6890 | female | 104 | 113 | 92 | 99 | 94 |
| tested | 6642 | female | 96 | 146 | 91 | 87 | 98 |
| substance | 6500 | female | 58 | 74 | 63 | 69 | 62 |
| (3375 mg/kg) n = 3 | Mean ± SD | | 86 ± 25 | 111 ± 36 | 82 ± 16 | 85 ± 15 | 85 ± 20 |
| GROUP C | 6043 | male | 56 | 81 | 74 | 84 | 86 |
| placebo | 6343 | male | 83 | 123 | 119 | 131 | 136 |
| group | 6347 | male | 56 | 74 | 66 | 74 | 72 |
| n = 5 | 6872 | female | 107 | 111 | 113 | 104 | 111 |
| | 6880 | female | 106 | 92 | 109 | 118 | 118 |
| | Mean ± SD | | 82 ± 25 | 96 ± 20 | 96 ± 24 | 102 ± 23 | 105 ± 26 |

Notes:
[a] 34 days before administration (D-34);

TABLE 6-12

Influence of administrating tested substance for 30 days on TBIL
(Mean ± SD)

| Group | Animal No. | fe/m | TBIL (μmol/L) baseline[a] | D0 | D10 | D20 | D30 |
|---|---|---|---|---|---|---|---|
| GROUP A | 6890 | female | 4.2 | 3.6 | 3.0 | 3.8 | 2.7 |
| tested | 6642 | female | 4.0 | 2.8 | 4.0 | 2.6 | 4.7 |
| substance | 6500 | female | 4.7 | 1.8 | 4.0 | 6.5 | 1.8 |
| (3375 mg/kg) n = 3 | Mean ± SD | | 4.3 ± 0.4 | 2.7 ± 0.9 | 3.7 ± 0.6 | 4.3 ± 2.0 | 3.1 ± 1.5 |
| GROUP C | 6043 | male | 3.3 | 2.9 | 2.5 | 2.7 | 2.7 |
| placebo | 6343 | male | 2.9 | 2.7 | 2.1 | 3.7 | 2.2 |
| group | 6347 | male | 2.8 | 4.6 | 5.7 | 5.0 | 4.1 |
| n = 5 | 6872 | female | 2.4 | 1.5 | 1.7 | 1.3 | 2.7 |
| | 6880 | female | 5.1 | 5.8 | 3.8 | 3.9 | 5.3 |
| | Mean ± SD | | 3.3 ± 1.1 | 3.5 ± 1.7 | 3.2 ± 1.6 | 3.3 ± 1.4 | 3.4 ± 1.3 |

Notes:
[a] 34 days before administration (D-34);

TABLE 6-13

Influence of administrating tested substance for 30 days on TP
(Mean ± SD)

| Group | Animal No. | fe/m | TP (g/L) baseline[a] | D0 | D10 | D20 | D30 |
|---|---|---|---|---|---|---|---|
| GROUP A | 6890 | female | 80.1 | 73.7 | 72.5 | 73.2 | 74.1 |
| tested | 6642 | female | 75.3 | 85.8 | 78.6 | 74.4 | 80.9 |
| substance | 6500 | female | 73.1 | 73.2 | 73.1 | 72.2 | 73.8 |
| (3375 mg/kg) n = 3 | Mean ± SD | | 76.2 ± 3.6 | 77.6 ± 7.1 | 74.7 ± 3.4 | 73.3 ± 1.1 | 76.3 ± 4.0 |
| GROUP C | 6043 | male | 70.1 | 67.9 | 69.1 | 70.3 | 70.4 |
| placebo | 6343 | male | 77.5 | 70.6 | 68.7 | 65.3 | 69.6 |
| group | 6347 | male | 77.8 | 78.3 | 76.8 | 76.2 | 78.5 |
| n = 5 | 6872 | female | 75.3 | 73.1 | 72.4 | 68.2 | 69.1 |
| | 6880 | female | 67.0 | 68.9 | 72.3 | 67.6 | 71.2 |
| | Mean ± SD | | 73.5 ± 4.8 | 71.8 ± 4.2 | 71.9 ± 3.3 | 69.5 ± 4.1 | 71.8 ± 3.9 |

Notes:
[a] 34 days before administration (D-34);

TABLE 6-14

Influence of administrating tested substance for 30 days on ALB
(Mean ± SD)

| | | | ALB (g/L) | | | | |
|---|---|---|---|---|---|---|---|
| Group | Animal No. | fe/m | baseline[a] | D0 | D10 | D20 | D30 |
| GROUP A | 6890 | female | 53.3 | 49.6 | 50.2 | 50.6 | 51.8 |
| tested | 6642 | female | 46.4 | 55.5 | 52.5 | 51.4 | 52.6 |
| substance | 6500 | female | 49.9 | 49.1 | 49.6 | 50.4 | 49.8 |
| (3375 mg/kg) | Mean ± SD | | | 49.9 ± 3.5 | 51.4 ± 3.6 | 50.8 ± 1.5 | 50.8 ± 0.5 | 51.4 ± 1.4 |
| n = 3 | | | | | | | |
| GROUP C | 6043 | male | 50.8 | 48.2 | 50.4 | 51.5 | 51.6 |
| placebo | 6343 | male | 48.0 | 44.7 | 43.8 | 44.0 | 46.0 |
| group | 6347 | male | 49.2 | 49.6 | 50.9 | 52.1 | 51.6 |
| n = 5 | 6872 | female | 45.7 | 44.0 | 45.6 | 42.9 | 43.4 |
| | 6880 | female | 44.3 | 45.0 | 47.6 | 46.2 | 46.1 |
| | Mean ± SD | | | 47.6 ± 2.6 | 46.3 ± 2.5 | 47.7 ± 3.0 | 47.3 ± 4.2 | 47.7 ± 3.7 |

Notes:
a34 days before administration (D-34);

TABLE 6-15

Influence of administrating tested substance for 30 days on BUN
(Mean ± SD)

| | | | BUN (μmol/L) | | | | |
|---|---|---|---|---|---|---|---|
| Group | Animal No. | fe/m | baseline[a] | D0 | D10 | D20 | D30 |
| GROUP A | 6890 | female | 6.9 | 5.3 | 6.4 | 5.5 | 5.4 |
| tested | 6642 | female | 6.4 | 3.6 | 4.3 | 4.1 | 3.2 |
| substance | 6500 | female | 8.8 | 5.3 | 6.2 | 6.3 | 6.3 |
| (3375 mg/kg) n = 3 | Mean ± SD | | | 7.4 ± 1.3 | 4.7 ± 1.0 | 5.6 ± 1.2 | 5.3 ± 1.1 | 5.0 ± 1.6 |
| GROUP C | 6043 | male | 9.2 | 6.1 | 5.9 | 6.1 | 5.5 |
| placebo | 6343 | male | 15.3 | 6.0 | 7.3 | 5.8 | 5.8 |
| group | 6347 | male | 4.4 | 5.6 | 6.8 | 5.6 | 5.3 |
| n = 5 | 6872 | female | 4.0 | 5.8 | 4.8 | 6.4 | 5.1 |
| | 6880 | female | 6.3 | 6.7 | 4.1 | 4.6 | 4.3 |
| | Mean ± SD | | | 7.8 ± 4.6 | 6.0 ± 0.4 | 5.8 ± 1.3 | 5.7 ± 0.7 | 5.2 ± 0.6 |

Notes:
[a]34 days before administration (D-34);

TABLE 6-16

Influence of administrating tested substance for 30 days on CR-S
(Mean ± SD)

| | | | CR-S (μmol/L) | | | | |
|---|---|---|---|---|---|---|---|
| Group | Animal No. | fe/m | baseline[a] | D0 | D10 | D20 | D30 |
| GROUP A | 6890 | female | 46 | 49 | 60 | 57 | 52 |
| tested | 6642 | female | 48 | 48 | 61 | 57 | 51 |
| substance | 6500 | female | 46 | 46 | 56 | 63 | 52 |
| (3375 mg/kg) n = 3 | Mean ± SD | | | 47 ± 1 | 48 ± 2 | 59 ± 3 | 59 ± 3 | 52 ± 1 |
| GROUP C placebo group | 6043 | male | 48 | 44 | 48 | 58 | 51 |
| n = 5 | 6343 | male | 67 | 53 | 50 | 49 | 51 |
| | 6347 | male | 40 | 64 | 65 | 62 | 58 |
| | 6872 | female | 33 | 35 | 44 | 42 | 42 |
| | 6880 | female | 45 | 45 | 56 | 47 | 54 |
| | Mean ± SD | | | 47 ± 13 | 48 ± 11 | 53 ± 8 | 52 ± 8 | 51 ± 6 |

Notes:
1. [a]34 days before administration (D-34);

TABLE 6-17

Influence of administrating tested substance for 30 days on CK
(Mean ± SD)

| Group | Animal No. | fe/m | baseline[a] | D0 | D10 | D20 | D30 |
|---|---|---|---|---|---|---|---|
| GROUP A | 6890 | female | 118 | 95 | 86 | 89 | 76 |
| tested | 6642 | female | 159 | 215 | 144 | 166 | 203 |
| substance | 6500 | female | 129 | 104 | 82 | 113 | 79 |
| (3375 mg/kg) | Mean ± SD | | 135 ± 21 | 138 ± 67 | 104 ± 35 | 123 ± 39 | 119 ± 72 |
| n = 3 | | | | | | | |
| GROUP C | 6043 | male | 194 | 118 | 137 | 111 | 140 |
| placebo | 6343 | male | 288 | 142 | 153 | 182 | 172 |
| group | 6347 | male | 185 | 89 | 76 | 104 | 103 |
| n = 5 | 6872 | female | 133 | 106 | 229 | 116 | 103 |
| | 6880 | female | 386 | 138 | 146 | 160 | 165 |
| | Mean ± SD | | 237 ± 100 | 119 ± 22 | 148 ± 55 | 135 ± 34 | 137 ± 33 |

Notes:
1. [a] 34 days before administration (D-34);

TABLE 6-18

Influence of administrating tested substance for 30 days on URIC
(Mean ± SD)

| Group | Animal No. | fe/m | baseline[a] | D0 | D10 | D20 | D30 |
|---|---|---|---|---|---|---|---|
| GROUP A | 6890 | female | 1 | 2 | 5 | 2 | 3 |
| tested | 6642 | female | 6 | 2 | 5 | 2 | 2 |
| substance | 6500 | female | 3 | 2 | 4 | 4 | 3 |
| (3375 mg/kg) | Mean ± SD | | 3 ± 3 | 2 ± 0 | 5 ± 1 | 3 ± 1 | 3 ± 1 |
| n = 3 | | | | | | | |
| GROUP C | 6043 | male | 2 | 3 | 5 | 4 | 3 |
| placebo | 6343 | male | 5 | 5 | 4 | 3 | 2 |
| group | 6347 | male | 3 | 4 | 6 | 5 | 3 |
| n = 5 | 6872 | female | 1 | 1 | 3 | 3 | 2 |
| | 6880 | female | 3 | 2 | 4 | 3 | 3 |
| | Mean ± SD | | 3 ± 1 | 3 ± 2 | 4 ± 1 | 4 ± 1 | 3 ± 1 |

Notes:
[a] 34 days before administration (D-34);

TABLE 6-19

Influence of administrating tested substance for 30 days on DBIL
(Mean ± SD)

| Group | Animal No. | fe/m | baseline[a] | D0 | D10 | D20 | D30 |
|---|---|---|---|---|---|---|---|
| GROUP A | 6890 | female | 1.5 | 1.2 | 0.3 | 1.3 | 1.4 |
| tested | 6642 | female | 1.4 | 0.8 | 1.1 | 1.0 | 2.0 |
| substance | 6500 | female | 1.6 | 0.9 | 1.3 | 2.7 | 1.6 |
| (3375 mg/kg) n = 3 | Mean ± SD | | 1.5 ± 0.1 | 1.0 ± 0.2 | 0.9 ± 0.5 | 1.7 ± 0.9 | 1.7 ± 0.3 |
| GROUP C | 6043 | male | 1.2 | 0.9 | 0.2 | 0.5 | 1.1 |
| placebo | 6343 | male | 1.1 | 0.8 | 0.4 | 1.0 | 1.1 |
| group | 6347 | male | 1.2 | 1.7 | 0.9 | 0.9 | 1.7 |
| n = 5 | 6872 | female | 0.8 | 0.7 | 0.8 | 0.5 | 0.9 |
| | 6880 | female | 1.7 | 1.8 | 1.1 | 1.4 | 1.6 |
| | Mean ± SD | | 1.2 ± 0.3 | 1.2 ± 0.5 | 0.7 ± 0.4 | 0.9 ± 0.4 | 1.3 ± 0.3 |

Notes:
1. [a] 34 days before administration (D-34);

TABLE 6-20

Influence of administrating tested substance for 30 days on FPG
(Mean ± SD)

| | | | FPG (mmol/L) | | | | |
|---|---|---|---|---|---|---|---|
| Group | Animal No. | fe/m | baseline[a] | D0 | D10 | D20 | D30 |
| GROUP A | 6890 | female | 4.82 | 4.56 | 4.11 | 5.05 | 4.48 |
| tested | 6642 | female | 3.32 | 5.30 | 5.43 | 6.00 | 5.18 |
| substance | 6500 | female | 4.56 | 4.52 | 3.75 | 6.14 | 4.75 |
| (3375 mg/kg) | Mean ± SD | | 4.23 ± 0.80 | 4.79 ± 0.44 | 4.43 ± 0.88 | 5.73 ± 0.59 | 4.80 ± 0.35 |
| n = 3 | | | | | | | |
| GROUP C | 6043 | male | 3.81 | 4.06 | 3.50 | 4.38 | 4.32 |
| placebo | 6343 | male | 5.59 | 4.59 | 3.98 | 3.87 | 3.92 |
| group | 6347 | male | 5.09 | 3.85 | 3.73 | 3.86 | 4.28 |
| n = 5 | 6872 | female | 4.64 | 4.14 | 4.04 | 4.78 | 4.15 |
| | 6880 | female | 4.54 | 2.74 | 4.57 | 4.16 | 4.57 |
| | Mean ± SD | | 4.73 ± 0.66 | 3.88 ± 0.69 | 3.96 ± 0.40 | 4.21 ± 0.39 | 4.25 ± 0.24 |

Notes:
[a] 34 days before administration (D-34);

TABLE 6-21

Influence of administrating tested substance for 30 days on FRA
(Mean ± SD)

| | | | FRA (µmol/L) | | | | |
|---|---|---|---|---|---|---|---|
| Group | Animal No. | fe/m | baseline[a] | D0 | D10 | D20 | D30 |
| GROUP A | 6890 | female | 218 | 196 | 178 | 199 | 190 |
| tested | 6642 | female | 219 | 236 | 207 | 219 | 220 |
| substance | 6500 | female | 207 | 207 | 188 | 224 | 196 |
| (3375 mg/kg) n = 3 | Mean ± SD | | 215 ± 7 | 213 ± 21 | 191 ± 15 | 214 ± 13 | 202 ± 16 |
| GROUP C | 6043 | male | 203 | 202 | 193 | 202 | 191 |
| placebo | 6343 | male | 205 | 204 | 199 | 194 | 191 |
| group | 6347 | male | 232 | 231 | 205 | 257 | 210 |
| n = 5 | 6872 | female | 199 | 189 | 166 | 187 | 183 |
| | 6880 | female | 183 | 191 | 196 | 182 | 198 |
| | Mean ± SD | | 204 ± 18 | 203 ± 17 | 192 ± 15 | 204 ± 30 | 195 ± 10 |

Notes:
[a] 34 days before administration (D-34);

TABLE 6-22

Influence of administrating tested substance for 30 days on TC
(Mean ± SD)

| | | | TC (mmol/L) | | | | |
|---|---|---|---|---|---|---|---|
| Group | Animal No. | fe/m | baseline[a] | D0 | D10 | D20 | D30 |
| GROUP A | 6890 | female | 3.06 | 3.34 | 2.83 | 2.73 | 2.54 |
| tested | 6642 | female | 2.68 | 4.24 | 3.26 | 3.17 | 3.84 |
| substance | 6500 | female | 1.98 | 2.29 | 2.31 | 2.72 | 2.36 |
| (3375 mg/kg) | Mean ± SD | | 2.57 ± 0.55 | 3.29 ± 0.98 | 2.80 ± 0.48 | 2.87 ± 0.26 | 2.91 ± 0.81 |
| n = 3 | | | | | | | |
| GROUP C | 6043 | male | 1.57 | 2.24 | 2.24 | 2.46 | 2.52 |
| placebo | 6343 | male | 3.89 | 3.70 | 3.26 | 3.39 | 3.13 |
| group | 6347 | male | 2.65 | 3.25 | 3.40 | 3.39 | 3.37 |
| n = 5 | 6872 | female | 2.44 | 2.47 | 2.81 | 2.63 | 2.92 |
| | 6880 | female | 2.37 | 2.85 | 3.38 | 3.09 | 3.29 |
| | Mean ± SD | | 2.58 ± 0.84 | 2.90 ± 0.59 | 3.02 ± 0.50 | 2.99 ± 0.43 | 3.05 ± 0.34 |

Notes:
[a] 34 days before administration (D-34);

TABLE 6-23

Influence of administrating tested substance for 30 days on LDL-c
(Mean ± SD)

| Group | Animal No. | fe/m | LDL-c (mmol/L) | | | | |
|---|---|---|---|---|---|---|---|
| | | | baseline[a] | D0 | D10 | D20 | D30 |
| GROUP A | 6890 | female | 1.60 | 1.76 | 1.41 | 1.42 | 1.20 |
| tested | 6642 | female | 1.29 | 1.92 | 1.25 | 1.30 | 1.60 |
| substance | 6500 | female | 1.02 | 0.96 | 0.96 | 1.21 | 0.75 |
| (3375 mg/kg) n = 3 | Mean ± SD | | 1.30 ± 0.29 | 1.55 ± 0.51 | 1.21 ± 0.23 | 1.31 ± 0.11 | 1.18 ± 0.43 |
| GROUP C | 6043 | male | 0.57 | 0.96 | 0.97 | 1.14 | 1.14 |
| placebo | 6343 | male | 2.10 | 1.78 | 1.60 | 1.73 | 1.27 |
| group | 6347 | male | 1.49 | 1.67 | 1.71 | 1.81 | 1.75 |
| n = 5 | 6872 | female | 1.32 | 1.22 | 1.47 | 1.41 | 1.45 |
| | 6880 | female | 1.48 | 1.65 | 1.99 | 1.85 | 1.99 |
| | Mean ± SD | | 1.39 ± 0.55 | 1.46 ± 0.35 | 1.55 ± 0.38 | 1.59 ± 0.30 | 1.52 ± 0.35 |

Notes:
[a] 34 days before administration (D-34);

TABLE 6-24

Influence of administrating tested substance for 30 days on HDL-c (Mean ± SD)

| Group | Animal No. | fe/m | HDL-c (mmol/L) | | | | |
|---|---|---|---|---|---|---|---|
| | | | baseline[a] | D0 | D10 | D20 | D30 |
| GROUP A | 6890 | female | 1.51 | 1.72 | 1.51 | 1.42 | 1.51 |
| tested | 6642 | female | 1.44 | 2.69 | 2.15 | 2.03 | 2.40 |
| substance | 6500 | female | 0.93 | 1.46 | 1.39 | 1.78 | 1.74 |
| (3375 mg/kg) n = 3 | Mean ± SD | | 1.29 ± 0.32 | 1.96 ± 0.65 | 1.68 ± 0.41 | 1.74 ± 0.31 | 1.88 ± 0.46 |
| GROUP C | 6043 | male | 1.06 | 1.26 | 1.24 | 1.38 | 1.57 |
| placebo | 6343 | male | 1.87 | 2.15 | 1.81 | 1.94 | 2.08 |
| group | 6347 | male | 1.38 | 1.83 | 1.84 | 1.81 | 1.91 |
| n = 5 | 6872 | female | 1.23 | 1.37 | 1.46 | 1.46 | 1.65 |
| | 6880 | female | 0.96 | 1.35 | 1.56 | 1.44 | 1.50 |
| | Mean ± SD | | 1.30 ± 0.36 | 1.59 ± 0.38 | 1.58 ± 0.25 | 1.61 ± 0.25 | 1.74 ± 0.24 |

Notes:
[a] 34 days before administration (D-34);

TABLE 6-25

Influence of administrating tested substance for 30 days on TG (Mean ± SD)

| Group | Animal No. | fe/m | TG (mmol/L) | | | | |
|---|---|---|---|---|---|---|---|
| | | | baseline[a] | D0 | D10 | D20 | D30 |
| GROUP A | 6890 | female | 0.57 | 0.42 | 0.58 | 0.63 | 0.62 |
| tested | 6642 | female | 0.60 | 0.44 | 0.45 | 0.49 | 0.48 |
| substance | 6500 | female | 0.67 | 0.68 | 0.80 | 0.27 | 0.65 |
| (3375 mg/kg) n = 3 | Mean ± SD | | 0.61 ± 0.05 | 0.51 ± 0.14 | 0.61 ± 0.18 | 0.46 ± 0.18 | 0.58 ± 0.09 |
| GROUP C | 6043 | male | 0.44 | 0.97 | 0.96 | 0.57 | 0.72 |
| placebo | 6343 | male | 0.56 | 0.50 | 0.52 | 0.39 | 0.36 |
| group | 6347 | male | 0.45 | 0.70 | 0.60 | 0.50 | 0.37 |
| n = 5 | 6872 | female | 0.48 | 0.52 | 0.48 | 0.55 | 0.70 |
| | 6880 | female | 0.75 | 0.79 | 0.40 | 0.43 | 0.42 |
| | Mean ± SD | | 0.54 ± 0.13 | 0.70 ± 0.20 | 0.59 ± 0.22 | 0.49 ± 0.08 | 0.51 ± 0.18 |

Notes:
[a] 34 days before administration (D-34);

5.3.4 Influence on Haematological Indexes

Influence of the tested substance on haematological in rhesus are shown in Table 6-26 to Table 6-53. There were no obvious abnormalities in the haematological indexes of the animals in the placebo group and the animals in the test group.

TABLE 6-26

Influence of administrating tested substance for 30 days on white cell (Mean ± SD)

| Group | Animal No. | fe/m | White cell WBC ($10^9$/L) | | | | |
|---|---|---|---|---|---|---|---|
| | | | baseline[a] | D0 | D10 | D20 | D30 |
| GROUP A | 6890 | female | 9.49 | 8.85 | 5.47 | 8.17 | 7.60 |
| tested | 6642 | female | 11.80 | 11.97 | 6.64 | 11.24 | 6.90 |
| substance | 6500 | female | 6.58 | 6.06 | 4.85 | 5.06 | 6.20 |
| (3375 mg/kg) | Mean ± SD | | 9.29 ± 2.62 | 8.96 ± 2.96 | 5.65 ± 0.91 | 8.16 ± 3.09 | 6.90 ± 0.70 |
| n = 3 | | | | | | | |
| GROUP C | 6043 | male | 9.62 | 6.45 | 6.06 | 6.75 | 5.78 |
| placebo | 6343 | male | 13.14 | 11.13 | 13.01 | 10.91 | 9.69 |
| group | 6347 | male | 7.57 | 7.00 | 5.15 | 6.32 | 4.41 |
| n = 5 | 6872 | female | 7.16 | 9.58 | 8.02 | 6.09 | 6.51 |
| | 6880 | female | 10.55 | 13.50 | 8.38 | 9.79 | 10.29 |
| | Mean ± SD | | 9.61 ± 2.42 | 9.53 ± 2.92 | 8.12 ± 3.04 | 7.97 ± 2.22 | 7.34 ± 2.55 |

Notes:
[a] 34 days before administration (D-34);

TABLE 6-27

Influence of administrating tested substance for 30 days on granulocytes, absolute (Mean ± SD)

| Group | Animal No. | fe/m | granulocytes, absolute GRAN ($10^9$/L) | | | | |
|---|---|---|---|---|---|---|---|
| | | | baseline[a] | D0 | D10 | D20 | D30 |
| GROUP A | 6890 | female | 4.64 | 3.93 | 2.08 | 3.14 | 3.40 |
| tested | 6642 | female | 5.69 | 5.68 | 2.45 | 5.05 | 2.17 |
| substance | 6500 | female | 2.77 | 2.01 | 1.60 | 1.83 | 2.84 |
| (3375 mg/kg) | Mean ± SD | | 4.37 ± 1.48 | 3.87 ± 1.84 | 2.04 ± 0.43 | 3.34 ± 1.62 | 2.80 ± 0.62 |
| n = 3 | | | | | | | |
| GROUP C | 6043 | male | 5.53 | 3.11 | 2.16 | 2.51 | 2.28 |
| placebo | 6343 | male | 4.37 | 1.91 | 4.96 | 2.20 | 1.11 |
| group | 6347 | male | 2.97 | 1.53 | 1.25 | 1.29 | 0.72 |
| n = 5 | 6872 | female | 3.78 | 4.55 | 4.79 | 2.43 | 2.62 |
| | 6880 | female | 4.45 | 5.67 | 1.61 | 2.36 | 3.67 |
| | Mean ± SD | | 4.22 ± 0.94 | 3.35 ± 1.75 | 2.95 ± 1.78 | 2.16 ± 0.50 | 2.08 ± 1.19 |

Notes:
[a] 34 days before administration (D-34);

TABLE 6-28

Influence of administrating tested substance for 30 days on lymphocytes, absolute (Mean ± SD)

| Group | Animal No. | fe/m | lymphocytes, absolute LYMF ($10^9$/L) | | | | |
|---|---|---|---|---|---|---|---|
| | | | baseline[a] | D0 | D10 | D20 | D30 |
| GROUP A | 6890 | female | 4.43 | 4.36 | 3.17 | 4.56 | 3.78 |
| tested | 6642 | female | 5.27 | 5.69 | 3.92 | 5.73 | 4.36 |
| substance | 6500 | female | 3.48 | 3.75 | 3.01 | 3.02 | 2.96 |
| (3375 mg/kg) | Mean ± SD | | 4.39 ± 0.90 | 4.60 ± 0.99 | 3.37 ± 0.49 | 4.44 ± 1.36 | 3.70 ± 0.70 |
| n = 3 | | | | | | | |
| GROUP C | 6043 | male | 3.45 | 2.92 | 3.38 | 3.74 | 3.12 |
| placebo | 6343 | male | 7.86 | 8.38 | 7.60 | 7.75 | 8.07 |
| group | 6347 | male | 4.14 | 4.92 | 3.52 | 4.63 | 3.39 |
| n = 5 | 6872 | female | 2.98 | 4.42 | 2.93 | 3.17 | 3.45 |
| | 6880 | female | 5.43 | 6.73 | 6.02 | 6.62 | 5.77 |
| | Mean ± SD | | 4.77 ± 1.96 | 5.47 ± 2.12 | 4.69 ± 2.03 | 5.18 ± 1.94 | 4.76 ± 2.14 |

Notes:
1. [a] 34 days before administration (D-34);

TABLE 6-29

Influence of administrating tested substance for 30 days on number of monocytes (Mean ± SD)

| Group | Animal No. | fe/m | number of monocytes ($10^9$/L) | | | | |
|---|---|---|---|---|---|---|---|
| | | | baseline[a] | D0 | D10 | D20 | D30 |
| GROUP A | 6890 | female | 0.20 | 0.28 | 0.06 | 0.22 | 0.17 |
| tested | 6642 | female | 0.33 | 0.30 | 0.09 | 0.22 | 0.16 |
| substance | 6500 | female | 0.12 | 0.09 | 0.04 | 0.05 | 0.08 |
| (3375 mg/kg) | Mean ± SD | | 0.22 ± 0.11 | 0.22 ± 0.12 | 0.06 ± 0.03 | 0.16 ± 0.10 | 0.14 ± 0.05 |
| n = 3 | | | | | | | |
| GROUP C | 6043 | male | 0.29 | 0.12 | 0.10 | 0.14 | 0.11 |
| placebo | 6343 | male | 0.53 | 0.44 | 0.22 | 0.43 | 0.19 |
| group | 6347 | male | 0.25 | 0.33 | 0.19 | 0.24 | 0.13 |
| n = 5 | 6872 | female | 0.21 | 0.17 | 0.13 | 0.21 | 0.19 |
| | 6880 | female | 0.24 | 0.38 | 0.18 | 0.29 | 0.22 |
| | Mean ± SD | | 0.30 ± 0.13 | 0.29 ± 0.14 | 0.16 ± 0.05* | 0.26 ± 0.11 | 0.17 ± 0.05 |

Notes:
1. [a]34 days before administration (D-34);

TABLE 6-30

Influence of administrating tested substance for 30 days on number of eosinophils (Mean ± SD)

| Group | Animal No. | fe/m | number of eosinophils ($10^9$/L) | | | | |
|---|---|---|---|---|---|---|---|
| | | | baseline[a] | D0 | D10 | D20 | D30 |
| GROUP A | 6890 | female | 0.12 | 0.21 | 0.10 | 0.18 | 0.19 |
| tested | 6642 | female | 0.30 | 0.16 | 0.11 | 0.11 | 0.11 |
| substance | 6500 | female | 0.14 | 0.16 | 0.17 | 0.12 | 0.28 |
| (3375 mg/kg) | Mean ± SD | | 0.19 ± 0.10 | 0.18 ± 0.03 | 0.13 ± 0.04 | 0.14 ± 0.04 | 0.19 ± 0.09 |
| n = 3 | | | | | | | |
| GROUP C | 6043 | male | 0.29 | 0.26 | 0.36 | 0.30 | 0.23 |
| placebo | 6343 | male | 0.08 | 0.26 | 0.16 | 0.41 | 0.21 |
| group | 6347 | male | 0.08 | 0.08 | 0.04 | 0.05 | 0.09 |
| n = 5 | 6872 | female | 0.15 | 0.38 | 0.12 | 0.22 | 0.22 |
| | 6880 | female | 0.35 | 0.59 | 0.46 | 0.37 | 0.50 |
| | Mean ± SD | | 0.19 ± 0.12 | 0.31 ± 0.19 | 0.23 ± 0.18 | 0.27 ± 0.14 | 0.25 ± 0.15 |

Notes:
1. [a]34 days before administration (D-34);

TABLE 6-31

Influence of administrating tested substance for 30 days on number of basophils (Mean ± SD)

| Group | Animal No. | fe/m | number of basophils ($10^9$/L) | | | | |
|---|---|---|---|---|---|---|---|
| | | | baseline[a] | D0 | D10 | D20 | D30 |
| GROUP A | 6890 | female | 0.02 | 0.01 | 0.00 | 0.01 | 0.01 |
| tested | 6642 | female | 0.03 | 0.02 | 0.00 | 0.01 | 0.01 |
| substance | 6500 | female | 0.01 | 0.01 | 0.00 | 0.00 | 0.00 |
| (3375 mg/kg) | Mean ± SD | | 0.02 ± 0.01 | 0.01 ± 0.01 | 0.00 ± 0.00 | 0.01 ± 0.01 | 0.01 ± 0.01 |
| n = 3 | | | | | | | |
| GROUP C | 6043 | male | 0.01 | 0.01 | 0.00 | 0.01 | 0.00 |
| placebo | 6343 | male | 0.03 | 0.03 | 0.01 | 0.01 | 0.02 |
| group | 6347 | male | 0.01 | 0.02 | 0.01 | 0.01 | 0.00 |
| n = 5 | 6872 | female | 0.00 | 0.01 | 0.01 | 0.00 | 0.00 |
| | 6880 | female | 0.00 | 0.01 | 0.01 | 0.02 | 0.02 |
| | Mean ± SD | | 0.01 ± 0.01 | 0.02 ± 0.01 | 0.01 ± 0.00 | 0.01 ± 0.01 | 0.01 ± 0.01 |

Notes:
1. [a]34 days before administration (D-34);

TABLE 6-32

Influence of administrating tested substance for 30 days on number of large unstained cells (Mean ± SD)

| Group | Animal No. | fe/m | number of large unstained cells LUC ($10^9$/L) | | | | |
|---|---|---|---|---|---|---|---|
| | | | baseline[a] | D0 | D10 | D20 | D30 |
| GROUP A | 6890 | female | 0.08 | 0.07 | 0.05 | 0.06 | 0.06 |
| tested | 6642 | female | 0.17 | 0.12 | 0.07 | 0.13 | 0.09 |
| substance | 6500 | female | 0.07 | 0.04 | 0.03 | 0.03 | 0.03 |
| (3375 mg/kg) | Mean ± SD | | 0.11 ± 0.06 | 0.08 ± 0.04 | 0.05 ± 0.02 | 0.07 ± 0.05 | 0.06 ± 0.03 |
| n = 3 | | | | | | | |
| GROUP C | 6043 | male | 0.05 | 0.03 | 0.05 | 0.05 | 0.04 |
| placebo | 6343 | male | 0.27 | 0.10 | 0.06 | 0.12 | 0.09 |
| group | 6347 | male | 0.12 | 0.11 | 0.14 | 0.09 | 0.07 |
| n = 5 | 6872 | female | 0.03 | 0.04 | 0.03 | 0.04 | 0.03 |
| | 6880 | female | 0.07 | 0.11 | 0.09 | 0.13 | 0.12 |
| | Mean ± SD | | 0.11 ± 0.10 | 0.08 ± 0.04 | 0.07 ± 0.04 | 0.09 ± 0.04 | 0.07 ± 0.04 |

Notes:
1. [a]34 days before administration (D-34);

TABLE 6-33

Influence of administrating tested substance for 30 days on neutrophil percentage (Mean ± SD)

| Group | Animal No. | fe/m | neutrophil percentage NEUT (%) | | | | |
|---|---|---|---|---|---|---|---|
| | | | baseline[a] | D0 | D10 | D20 | D30 |
| GROUP A | 6890 | female | 48.9 | 44.4 | 38.0 | 38.5 | 44.7 |
| tested | 6642 | female | 48.2 | 47.4 | 37.0 | 44.9 | 31.4 |
| substance | 6500 | female | 42.1 | 33.2 | 33.0 | 36.2 | 45.9 |
| (3375 mg/kg) | Mean ± SD | | 46.4 ± 3.7 | 41.7 ± 7.5 | 36.0 ± 2.6 | 39.9 ± 4.5 | 40.7 ± 8.0 |
| n = 3 | | | | | | | |
| GROUP C | 6043 | male | 57.5 | 48.3 | 35.7 | 37.2 | 39.5 |
| placebo | 6343 | male | 33.3 | 17.2 | 38.1 | 20.1 | 11.4 |
| group | 6347 | male | 39.3 | 21.9 | 24.3 | 20.4 | 16.4 |
| n = 5 | 6872 | female | 52.8 | 47.5 | 59.7 | 39.9 | 40.2 |
| | 6880 | female | 42.2 | 42.0 | 19.2 | 24.1 | 35.7 |
| | Mean ± SD | | 45.0 ± 9.9 | 35.4 ± 14.7 | 35.4 ± 15.7 | 28.3 ± 9.5 | 28.6 ± 13.7 |

Notes:
1. [a]34 days before administration (D-34);

TABLE 6-34

Influence of administrating tested substance for 30 days on lymphocyte percentage (Mean ± SD)

| Group | Animal No. | fe/m | lymphocyte percentage LYMPH (%) | | | | |
|---|---|---|---|---|---|---|---|
| | | | baseline[a] | D0 | D10 | D20 | D30 |
| GROUP A | 6890 | female | 46.7 | 49.2 | 58.1 | 55.8 | 49.7 |
| tested | 6642 | female | 44.7 | 47.6 | 59.0 | 51.0 | 63.1 |
| substance | 6500 | female | 52.8 | 61.9 | 62.1 | 59.7 | 47.8 |
| (3375 mg/kg) | Mean ± SD | | 48.1 ± 4.2 | 52.9 ± 7.8 | 59.7 ± 2.1 | 55.5 ± 4.4 | 53.5 ± 8.3 |
| n = 3 | | | | | | | |
| GROUP C | 6043 | male | 35.8 | 45.3 | 55.8 | 55.3 | 54.0 |
| placebo | 6343 | male | 59.8 | 75.3 | 58.4 | 71.0 | 83.2 |
| group | 6347 | male | 54.8 | 70.4 | 68.4 | 73.2 | 76.8 |
| n = 5 | 6872 | female | 41.6 | 46.2 | 36.6 | 52.2 | 53.0 |
| | 6880 | female | 51.5 | 49.9 | 71.9 | 67.6 | 56.1 |
| | Mean ± SD | | 48.7 ± 9.8 | 57.4 ± 14.3 | 58.2 ± 13.8 | 63.9 ± 9.5 | 64.6 ± 14.3 |

Notes:
1. [a]34 days before administration (D-34);

TABLE 6-35

Influence of administrating tested substance for 30 days on monocyte percentage (Mean ± SD)

| Group | Animal No. | fe/m | monocyte percentage MONO (%) | | | | |
| --- | --- | --- | --- | --- | --- | --- | --- |
| | | | baseline[a] | D0 | D10 | D20 | D30 |
| GROUP A | 6890 | female | 2.1 | 3.1 | 1.2 | 2.6 | 2.2 |
| tested | 6642 | female | 2.8 | 2.5 | 1.3 | 1.9 | 2.3 |
| substance | 6500 | female | 1.8 | 1.5 | 0.8 | 1.1 | 1.3 |
| (3375 mg/kg) | Mean ± SD | | 2.2 ± 0.5 | 2.4 ± 0.8 | 1.1 ± 0.3 | 1.9 ± 0.8 | 1.9 ± 0.6 |
| n = 3 | | | | | | | |
| GROUP C | 6043 | male | 3.0 | 1.9 | 1.7 | 2.1 | 1.8 |
| placebo | 6343 | male | 4.0 | 4.0 | 1.7 | 3.9 | 2.0 |
| group | 6347 | male | 3.3 | 4.8 | 3.7 | 3.8 | 3.0 |
| n = 5 | 6872 | female | 2.9 | 1.7 | 1.7 | 3.5 | 2.9 |
| | 6880 | female | 2.2 | 2.8 | 2.2 | 3.0 | 2.1 |
| | Mean ± SD | | 3.1 ± 0.7 | 3.0 ± 1.3 | 2.2 ± 0.9 | 3.3 ± 0.7 | 2.4 ± 0.6 |

Notes:
1. [a]34 days before administration (D-34);

TABLE 6-36

Influence of administrating tested substance for 30 days on eosinophils percentage (Mean ± SD)

| Group | Animal No. | fe/m | eosinophils percentage EOS (%) | | | | |
| --- | --- | --- | --- | --- | --- | --- | --- |
| | | | baseline[a] | D0 | D10 | D20 | D30 |
| GROUP A | 6890 | female | 1.3 | 2.4 | 1.9 | 2.2 | 2.4 |
| tested | 6642 | female | 2.5 | 1.3 | 1.6 | 1.0 | 1.6 |
| substance | 6500 | female | 2.1 | 2.6 | 3.5 | 2.3 | 4.5 |
| (3375 mg/kg) | Mean ± SD | | 2.0 ± 0.6 | 2.1 ± 0.7 | 2.3 ± 1.0 | 1.8 ± 0.7 | 2.8 ± 1.5 |
| n = 3 | | | | | | | |
| GROUP C | 6043 | male | 3.0 | 4.0 | 5.9 | 4.4 | 4.0 |
| placebo | 6343 | male | 0.6 | 2.3 | 1.2 | 3.8 | 2.2 |
| group | 6347 | male | 1.0 | 1.1 | 0.8 | 0.9 | 2.0 |
| n = 5 | 6872 | female | 2.1 | 4.0 | 1.5 | 3.7 | 3.4 |
| | 6880 | female | 3.3 | 4.4 | 5.4 | 3.8 | 4.9 |
| | Mean ± SD | | 2.0 ± 1.2 | 3.2 ± 1.4 | 3.0 ± 2.5 | 3.3 ± 1.4 | 3.3 ± 1.2 |

Notes:
1. [a]34 days before administration (D-34);

TABLE 6-37

Influence of administrating tested substance for 30 days on basophils percentage (Mean ± SD)

| Group | Animal No. | fe/m | basophils percentage BASO (%) | | | | |
| --- | --- | --- | --- | --- | --- | --- | --- |
| | | | baseline[a] | D0 | D10 | D20 | D30 |
| GROUP A | 6890 | female | 0.2 | 0.1 | 0.0 | 0.1 | 0.1 |
| tested | 6642 | female | 0.3 | 0.2 | 0.1 | 0.1 | 0.2 |
| substance | 6500 | female | 0.1 | 0.1 | 0.0 | 0.1 | 0.0 |
| (3375 mg/kg) | Mean ± SD | | 0.2 ± 0.1 | 0.1 ± 0.1 | 0.0 ± 0.1 | 0.1 ± 0.0 | 0.1 ± 0.1 |
| n = 3 | | | | | | | |
| GROUP C | 6043 | male | 0.1 | 0.1 | 0.0 | 0.2 | 0.1 |
| placebo | 6343 | male | 0.2 | 0.3 | 0.1 | 0.1 | 0.2 |
| group | 6347 | male | 0.1 | 0.3 | 0.3 | 0.2 | 0.1 |
| n = 5 | 6872 | female | 0.0 | 0.1 | 0.1 | 0.1 | 0.0 |
| | 6880 | female | 0.0 | 0.1 | 0.1 | 0.2 | 0.2 |
| | Mean ± SD | | 0.1 ± 0.1 | 0.2 ± 0.1 | 0.1 ± 0.1 | 0.2 ± 0.1 | 0.1 ± 0.1 |

Notes:
1. [a]34 days before administration (D-34);

TABLE 6-38

Influence of administrating tested substance for 30 days on large unstained cell percentage (Mean ± SD)

| | | | large unstained cell percentage LUC (%) | | | | |
|---|---|---|---|---|---|---|---|
| Group | Animal No. | fe/m | baseline[a] | D0 | D10 | D20 | D30 |
| GROUP A | 6890 | female | 0.9 | 0.8 | 0.8 | 0.8 | 0.8 |
| tested | 6642 | female | 1.5 | 1.0 | 1.0 | 1.2 | 1.3 |
| substance | 6500 | female | 1.1 | 0.7 | 0.7 | 0.6 | 0.4 |
| (3375 mg/kg) | Mean ± SD | | 1.2 ± 0.3 | 0.8 ± 0.2 | 0.8 ± 0.2 | 0.9 ± 0.3 | 0.8 ± 0.5 |
| n = 3 | | | | | | | |
| GROUP C | 6043 | male | 0.6 | 0.4 | 0.9 | 0.7 | 0.7 |
| placebo | 6343 | male | 2.0 | 0.9 | 0.5 | 1.1 | 0.9 |
| group | 6347 | male | 1.6 | 1.6 | 2.7 | 1.4 | 1.7 |
| n = 5 | 6872 | female | 0.5 | 0.5 | 0.4 | 0.7 | 0.5 |
| | 6880 | female | 0.7 | 0.8 | 1.1 | 1.3 | 1.2 |
| | Mean ± SD | | 1.1 ± 0.7 | 0.8 ± 0.5 | 1.1 ± 0.9 | 1.0 ± 0.3 | 1.0 ± 0.5 |

Notes:
1. [a]34 days before administration (D-34);

TABLE 6-39

Influence of administrating tested substance for 30 days on red cells (Mean ± SD)

| | | | Red cells RBC ($10^{12}$/L) | | | | |
|---|---|---|---|---|---|---|---|
| Group | Animal No. | fe/m | baseline[a] | D0 | D10 | D20 | D30 |
| GROUP A | 6890 | female | 5.54 | 5.42 | 5.67 | 5.31 | 5.25 |
| tested | 6642 | female | 5.12 | 5.92 | 5.01 | 5.00 | 4.64 |
| substance | 6500 | female | 5.49 | 5.33 | 4.98 | 5.21 | 4.98 |
| (3375 mg/kg) | Mean ± SD | | 5.38 ± 0.23 | 5.56 ± 0.32 | 5.22 ± 0.39 | 5.17 ± 0.16 | 4.96 ± 0.31 |
| n = 3 | | | | | | | |
| GROUP C | 6043 | male | 4.50 | 5.40 | 5.43 | 5.62 | 5.40 |
| placebo | 6343 | male | 5.16 | 4.84 | 5.06 | 4.93 | 5.18 |
| group | 6347 | male | 5.43 | 6.06 | 5.62 | 5.62 | 5.61 |
| n = 5 | 6872 | female | 5.16 | 5.41 | 5.35 | 5.16 | 5.18 |
| | 6880 | female | 5.67 | 5.58 | 5.75 | 5.81 | 5.93 |
| | Mean ± SD | | 5.18 ± 0.44 | 5.46 ± 0.44 | 5.44 ± 0.27 | 5.43 ± 0.37 | 5.46 ± 0.32 |

Notes:
1. [a]34 days before administration (D-34);

TABLE 6-40

Influence of administrating tested substance for 30 days on hemoglobin concentration (Mean ± SD)

| | | | Hemoglobin concentration HGB (g/L) | | | | |
|---|---|---|---|---|---|---|---|
| Group | Animal No. | fe/m | baseline[a] | D0 | D10 | D20 | D30 |
| GROUP A | 6890 | female | 138 | 134 | 143 | 134 | 131 |
| tested | 6642 | female | 137 | 159 | 138 | 137 | 128 |
| substance | 6500 | female | 129 | 126 | 121 | 128 | 124 |
| (3375 mg/kg) | Mean ± SD | | 135 ± 5 | 140 ± 17 | 134 ± 12 | 133 ± 5 | 128 ± 4 |
| n = 3 | | | | | | | |
| GROUP C | 6043 | male | 122 | 126 | 128 | 132 | 127 |
| placebo | 6343 | male | 130 | 123 | 130 | 124 | 130 |
| group | 6347 | male | 138 | 150 | 145 | 143 | 142 |
| n = 5 | 6872 | female | 125 | 131 | 130 | 126 | 127 |
| | 6880 | female | 140 | 142 | 146 | 146 | 149 |
| | Mean ± SD | | 131 ± 8 | 134 ± 11 | 136 ± 9 | 134 ± 10 | 135 ± 10 |

Notes:
1. [a]34 days before administration (D-34);

TABLE 6-41

Influence of administrating tested substance for 30 days on hematocrit (Mean ± SD)

| Group | Animal No. | fe/m | Hematocrit HCT (fL) | | | | |
|---|---|---|---|---|---|---|---|
| | | | baseline[a] | D0 | D10 | D20 | D30 |
| GROUP A | 6890 | female | 41.5 | 40.0 | 41.3 | 38.8 | 39.1 |
| tested | 6642 | female | 43.3 | 48.6 | 40.0 | 39.3 | 38.4 |
| substance | 6500 | female | 38.4 | 37.7 | 35.1 | 37.2 | 36.1 |
| (3375 mg/kg) | Mean ± SD | | 41.1 ± 2.5 | 42.1 ± 5.7 | 38.8 ± 3.3 | 38.4 ± 1.1 | 37.9 ± 1.6 |
| n = 3 | | | | | | | |
| GROUP C | 6043 | male | 33.7 | 39.4 | 39.3 | 40.6 | 39.9 |
| placebo | 6343 | male | 42.3 | 40.3 | 40.3 | 38.6 | 41.5 |
| group | 6347 | male | 42.9 | 47.9 | 42.8 | 43.0 | 44.1 |
| n = 5 | 6872 | female | 37.8 | 39.4 | 38.0 | 36.7 | 37.5 |
| | 6880 | female | 43.4 | 43.4 | 43.6 | 42.2 | 44.3 |
| | Mean ± SD | | 40.0 ± 4.2 | 42.1 ± 3.6 | 40.8 ± 2.4 | 40.2 ± 2.6 | 41.5 ± 2.9 |

Notes:
1. [a]34 days before administration (D-34);

TABLE 6-42

Influence of administrating tested substance for 30 days on mean corpuscular volume (Mean ± SD)

| Group | Animal No. | fe/m | Mean corpuscular volume MCV (fL) | | | | |
|---|---|---|---|---|---|---|---|
| | | | baseline[a] | D0 | D10 | D20 | D30 |
| GROUP A | 6890 | female | 74.9 | 73.8 | 72.9 | 73.1 | 74.5 |
| tested | 6642 | female | 84.5 | 82.0 | 79.9 | 78.6 | 82.8 |
| substance | 6500 | female | 70.1 | 70.8 | 70.4 | 71.4 | 72.5 |
| (3375 mg/kg) | Mean ± SD | | 76.5 ± 7.3 | 75.5 ± 5.8 | 74.4 ± 4.9 | 74.4 ± 3.8 | 76.6 ± 5.5 |
| n = 3 | | | | | | | |
| GROUP C | 6043 | male | 74.9 | 72.8 | 72.4 | 72.3 | 74.0 |
| placebo | 6343 | male | 82.0 | 83.4 | 79.7 | 78.2 | 80.1 |
| group | 6347 | male | 79.0 | 79.0 | 76.2 | 76.6 | 78.6 |
| n = 5 | 6872 | female | 73.4 | 72.8 | 71.1 | 71.1 | 72.3 |
| | 6880 | female | 76.5 | 77.8 | 75.9 | 72.6 | 74.8 |
| | Mean ± SD | | 77.2 ± 3.4 | 77.2 ± 4.5 | 75.1 ± 3.4 | 74.2 ± 3.1 | 76.0 ± 3.3 |

Notes:
1. [a]34 days before administration (D-34);

TABLE 6-43

Influence of administrating tested substance for 30 days on mean corpuscular hemoglobin (Mean ± SD)

| Group | Animal No. | fe/m | Mean corpuscular hemoglobin MCH (pg) | | | | |
|---|---|---|---|---|---|---|---|
| | | | baseline[a] | D0 | D10 | D20 | D30 |
| GROUP A | 6890 | female | 24.9 | 24.8 | 25.2 | 25.2 | 25.0 |
| tested | 6642 | female | 26.7 | 26.9 | 27.5 | 27.4 | 27.6 |
| substance | 6500 | female | 23.5 | 23.6 | 24.2 | 24.5 | 24.8 |
| (3375 mg/kg) | Mean ± SD | | 25.0 ± 1.6 | 25.1 ± 1.7 | 25.6 ± 1.7 | 25.7 ± 1.5 | 25.8 ± 1.6 |
| n = 3 | | | | | | | |
| GROUP C | 6043 | male | 27.1 | 23.3 | 23.6 | 23.5 | 23.5 |
| placebo | 6343 | male | 25.1 | 25.4 | 25.6 | 25.2 | 25.1 |
| group | 6347 | male | 25.3 | 24.8 | 25.7 | 25.4 | 25.2 |
| n = 5 | 6872 | female | 24.2 | 24.2 | 24.3 | 24.4 | 24.5 |
| | 6880 | female | 24.6 | 25.4 | 25.4 | 25.2 | 25.1 |
| | Mean ± SD | | 25.3 ± 1.1 | 24.6 ± 0.9 | 24.9 ± 0.9 | 24.7 ± 0.8 | 24.7 ± 0.7 |

Notes:
1. [a]34 days before administration (D-34);

TABLE 6-44

Influence of administrating tested substance for 30 days on mean corpuscular hemoglobin concentration (Mean ± SD)

| Group | Animal No. | fe/m | \multicolumn{5}{c}{Mean corpuscular hemoglobin concentration MCHC (g/l)} |
|---|---|---|---|---|---|---|---|
| | | | baseline[a] | D0 | D10 | D20 | D30 |
| GROUP A | 6890 | female | 332 | 336 | 346 | 344 | 336 |
| tested | 6642 | female | 316 | 328 | 345 | 349 | 334 |
| substance | 6500 | female | 335 | 334 | 344 | 343 | 342 |
| (3375 mg/kg) | Mean ± SD | | 328 ± 10 | 333 ± 4 | 345 ± 1 | 345 ± 3 | 337 ± 4 |
| n = 3 | | | | | | | |
| GROUP C | 6043 | male | 362 | 320 | 326 | 324 | 317 |
| placebo | 6343 | male | 306 | 305 | 322 | 323 | 313 |
| group | 6347 | male | 321 | 314 | 338 | 332 | 321 |
| n = 5 | 6872 | female | 330 | 332 | 341 | 343 | 338 |
| | 6880 | female | 322 | 326 | 335 | 347 | 335 |
| | Mean ± SD | | 328 ± 21 | 319 ± 10 | 332 ± 8 | 334 ± 11 | 325 ± 11 |

Notes:
1. [a] 34 days before administration (D-34);

TABLE 6-45

Influence of administrating tested substance for 30 days on red blood cell distribution width (Mean ± SD)

| Group | Animal No. | fe/m | \multicolumn{5}{c}{Red blood cell distribution width RDW (%)} |
|---|---|---|---|---|---|---|---|
| | | | baseline[a] | D0 | D10 | D20 | D30 |
| GROUP A | 6890 | female | 12.6 | 12.4 | 12.4 | 12.8 | 12.9 |
| tested | 6642 | female | 12.5 | 12.0 | 12.2 | 12.6 | 13.6 |
| substance | 6500 | female | 12.2 | 12.4 | 13.0 | 13.4 | 13.1 |
| (3375 mg/kg) | Mean ± SD | | 12.4 ± 0.2 | 12.3 ± 0.2 | 12.5 ± 0.4 | 12.9 ± 0.4 | 13.2 ± 0.4 |
| n = 3 | | | | | | | |
| GROUP C | 6043 | male | 12.4 | 11.6 | 11.8 | 11.5 | 11.6 |
| placebo | 6343 | male | 14.0 | 12.0 | 11.9 | 12.1 | 12.1 |
| group | 6347 | male | 13.8 | 12.1 | 11.9 | 11.8 | 12.1 |
| n = 5 | 6872 | female | 12.0 | 11.5 | 11.9 | 11.4 | 12.1 |
| | 6880 | female | 12.5 | 11.8 | 12.0 | 11.8 | 11.7 |
| | Mean ± SD | | 12.9 ± 0.9 | 11.8 ± 0.3 | 11.9 ± 0.1 | 11.7 ± 0.3 | 11.9 ± 0.2 |

Notes:
1. [a] 34 days before administration (D-34);

TABLE 6-46

Influence of administrating tested substance for 30 days on mean HGB distribution width (Mean ± SD)

| Group | Animal No. | fe/m | \multicolumn{5}{c}{Mean HGB distribution width HDW (g/l)} |
|---|---|---|---|---|---|---|---|
| | | | baseline[a] | D0 | D10 | D20 | D30 |
| GROUP A | 6890 | female | 20.8 | 21.9 | 21.0 | 22.0 | 22.5 |
| tested | 6642 | female | 21.0 | 22.0 | 22.6 | 23.9 | 23.2 |
| substance | 6500 | female | 22.6 | 23.0 | 22.7 | 22.9 | 24.3 |
| (3375 mg/kg) | Mean ± SD | | 21.5 ± 1.0 | 22.3 ± 0.6 | 22.1 ± 1.0 | 22.9 ± 1.0 | 23.3 ± 0.9 |
| n = 3 | | | | | | | |
| GROUP C | 6043 | male | 19.4 | 20.3 | 20.1 | 19.7 | 20.5 |
| placebo | 6343 | male | 18.4 | 18.6 | 18.4 | 18.5 | 18.7 |
| group | 6347 | male | 20.6 | 20.5 | 21.1 | 21.3 | 21.6 |
| n = 5 | 6872 | female | 22.3 | 23.0 | 23.2 | 23.9 | 23.9 |
| | 6880 | female | 20.2 | 21.4 | 20.9 | 22.0 | 21.5 |
| | Mean ± SD | | 20.2 ± 1.5 | 20.8 ± 1.6 | 20.7 ± 1.7 | 21.1 ± 2.1 | 21.2 ± 1.9 |

Notes:
1. [a] 34 days before administration (D-34);

TABLE 6-47

Influence of administrating tested substance for 30 days on mean RBC hemoglobin concentration (Mean ± SD)

| Group | Animal No. | fe/m | Mean RBC hemoglobin concentration CHCM (g/l) | | | | |
|---|---|---|---|---|---|---|---|
| | | | baseline[a] | D0 | D10 | D20 | D30 |
| GROUP A | 6890 | female | 316 | 328 | 333 | 332 | 329 |
| tested | 6642 | female | 298 | 320 | 331 | 339 | 320 |
| substance | 6500 | female | 322 | 334 | 336 | 337 | 333 |
| (3375 mg/kg) | Mean ± SD | | 312 ± 12 | 327 ± 7 | 333 ± 3 | 336 ± 4 | 327 ± 7 |
| n = 3 | | | | | | | |
| GROUP C | 6043 | male | 295 | 310 | 314 | 312 | 302 |
| placebo | 6343 | male | 288 | 287 | 304 | 307 | 298 |
| group | 6347 | male | 305 | 307 | 320 | 314 | 306 |
| n = 5 | 6872 | female | 316 | 327 | 335 | 331 | 325 |
| | 6880 | female | 306 | 311 | 319 | 337 | 320 |
| | Mean ± SD | | 302 ± 11 | 308 ± 14 | 318 ± 11 | 320 ± 13 | 310 ± 12 |

Notes:
1. [a]34 days before administration (D-34);

TABLE 6-48

Influence of administrating tested substance for 30 days on mean RBC hemoglobin content (Mean ± SD)

| Group | Animal No. | fe/m | Mean RBC hemoglobin content CH (Pg) | | | | |
|---|---|---|---|---|---|---|---|
| | | | baseline[a] | D0 | D10 | D20 | D30 |
| GROUP A | 6890 | female | 23.6 | 24.2 | 24.2 | 24.2 | 24.5 |
| tested | 6642 | female | 25.1 | 26.2 | 26.4 | 26.5 | 26.3 |
| substance | 6500 | female | 22.5 | 23.6 | 23.6 | 24.0 | 24.1 |
| (3375 mg/kg) | Mean ± SD | | 23.7 ± 1.3 | 24.7 ± 1.4 | 24.7 ± 1.5 | 24.9 ± 1.4 | 25.0 ± 1.2 |
| n = 3 | | | | | | | |
| GROUP C | 6043 | male | 22.1 | 22.5 | 22.7 | 22.5 | 22.3 |
| placebo | 6343 | male | 23.5 | 23.9 | 24.2 | 24.0 | 23.9 |
| group | 6347 | male | 24.0 | 24.2 | 24.3 | 24.0 | 24.0 |
| n = 5 | 6872 | female | 23.2 | 23.7 | 23.8 | 23.5 | 23.4 |
| | 6880 | female | 23.4 | 24.1 | 24.2 | 24.4 | 23.9 |
| | Mean ± SD | | 23.2 ± 0.7 | 23.7 ± 0.7 | 23.8 ± 0.7 | 23.7 ± 0.7 | 23.5 ± 0.7 |

Notes:
1. [a]34 days before administration (D-34);

TABLE 6-49

Influence of administrating tested substance for 30 days on red blood cell CH distribution width (Mean ± SD)

| Group | Animal No. | fe/m | Red blood cell CH distribution width CHDW (Pg) | | | | |
|---|---|---|---|---|---|---|---|
| | | | baseline[a] | D0 | D10 | D20 | D30 |
| GROUP A | 6890 | female | 3.07 | 3.14 | 3.15 | 3.20 | 3.27 |
| tested | 6642 | female | 3.26 | 3.22 | 3.32 | 3.37 | 3.38 |
| substance | 6500 | female | 2.98 | 3.23 | 3.24 | 3.38 | 3.36 |
| (3375 mg/kg) | Mean ± SD | | 3.10 ± 0.14 | 3.20 ± 0.05 | 3.24 ± 0.09 | 3.32 ± 0.10 | 3.34 ± 0.06 |
| n = 3 | | | | | | | |
| GROUP C | 6043 | male | 2.70 | 2.67 | 2.72 | 2.64 | 2.65 |
| placebo | 6343 | male | 3.26 | 3.05 | 3.01 | 3.01 | 2.97 |
| group | 6347 | male | 3.31 | 3.03 | 2.98 | 2.95 | 2.94 |
| n = 5 | 6872 | female | 3.03 | 3.05 | 3.11 | 2.99 | 3.03 |
| | 6880 | female | 3.21 | 3.15 | 3.21 | 3.24 | 3.10 |
| | Mean ± SD | | 3.10 ± 0.25 | 2.99 ± 0.18 | 3.01 ± 0.18 | 2.97 ± 0.21 | 2.94 ± 0.17 |

Notes:
1. [a]34 days before administration (D-34);

TABLE 6-50

Influence of administrating tested substance for 30 days on platelet (Mean ± SD)

| Group | Animal No. | fe/m | Platelet PLT ($10^9$/L) | | | | |
|---|---|---|---|---|---|---|---|
| | | | baseline[a] | D0 | D10 | D20 | D30 |
| GROUP A | 6890 | female | 405 | 463 | 554 | 469 | 459 |
| tested | 6642 | female | 478 | 501 | 493 | 364 | 422 |
| substance | 6500 | female | 356 | 394 | 389 | 393 | 431 |
| (3375 mg/kg) | Mean ± SD | | 413 ± 61 | 453 ± 54 | 479 ± 83 | 409 ± 54 | 437 ± 19 |
| n = 3 | | | | | | | |
| GROUP C | 6043 | male | 252 | 351 | 284 | 314 | 339 |
| placebo | 6343 | male | 312 | 322 | 358 | 278 | 406 |
| group | 6347 | male | 285 | 344 | 322 | 315 | 348 |
| n = 5 | 6872 | female | 344 | 379 | 322 | 283 | 243 |
| | 6880 | female | 377 | 304 | 317 | 281 | 310 |
| | Mean ± SD | | 314 ± 49 | 340 ± 29 | 321 ± 26 | 294 ± 19 | 329 ± 59 |

Notes:
1. [a] 34 days before administration (D-34);

TABLE 6-51

Influence of administrating tested substance for 30 days on plateletcrit (Mean ± SD)

| Group | Animal No. | fe/m | Plateletcrit PCT (%) | | | | |
|---|---|---|---|---|---|---|---|
| | | | baseline[a] | D0 | D10 | D20 | D30 |
| GROUP A | 6890 | female | 0.35 | 0.39 | 0.44 | 0.37 | 0.39 |
| tested | 6642 | female | 0.44 | 0.44 | 0.40 | 0.32 | 0.35 |
| substance | 6500 | female | 0.28 | 0.33 | 0.32 | 0.30 | 0.34 |
| (3375 mg/kg) | Mean ± SD | | 0.36 ± 0.08 | 0.39 ± 0.06 | 0.39 ± 0.06 | 0.33 ± 0.04 | 0.36 ± 0.03 |
| n = 3 | | | | | | | |
| GROUP C | 6043 | male | 0.19 | 0.25 | 0.21 | 0.22 | 0.25 |
| placebo | 6343 | male | 0.29 | 0.31 | 0.30 | 0.28 | 0.37 |
| group | 6347 | male | 0.28 | 0.37 | 0.32 | 0.33 | 0.34 |
| n = 5 | 6872 | female | 0.29 | 0.31 | 0.30 | 0.28 | 0.23 |
| | 6880 | female | 0.30 | 0.26 | 0.27 | 0.22 | 0.26 |
| | Mean ± SD | | 0.27 ± 0.05 | 0.30 ± 0.05 | 0.28 ± 0.04 | 0.27 ± 0.05 | 0.29 ± 0.06 |

Notes:
1. [a] 34 days before administration (D-34);

TABLE 6-52

Influence of administrating tested substance for 30 days on platelet distribution width (Mean ± SD)

| Group | Animal No. | fe/m | Platelet distribution width PDW (%) | | | | |
|---|---|---|---|---|---|---|---|
| | | | baseline[a] | D0 | D10 | D20 | D30 |
| GROUP A | 6890 | female | 57.9 | 55.1 | 49.0 | 48.4 | 49.5 |
| tested | 6642 | female | 55.6 | 55.4 | 46.0 | 51.5 | 45.5 |
| substance | 6500 | female | 49.4 | 49.4 | 51.1 | 49.7 | 48.1 |
| (3375 mg/kg) | Mean ± SD | | 54.3 ± 4.4 | 53.3 ± 3.4 | 48.7 ± 2.6 | 49.9 ± 1.6 | 47.7 ± 2.0 |
| n = 3 | | | | | | | |
| GROUP C | 6043 | male | 55.5 | 50.3 | 48.4 | 58.3 | 52.5 |
| placebo | 6343 | male | 52.4 | 53.5 | 57.1 | 52.2 | 51.2 |
| group | 6347 | male | 68.8 | 77.6 | 68.1 | 76.8 | 67.3 |
| n = 5 | 6872 | female | 54.9 | 56.5 | 67.7 | 68.3 | 63.6 |
| | 6880 | female | 55.2 | 65.8 | 62.5 | 54.8 | 60.4 |
| | Mean ± SD | | 57.4 ± 6.5 | 60.7 ± 11.1 | 60.8 ± 8.2 | 62.1 ± 10.3 | 59.0 ± 7.0 |

Notes:
1. [a] 34 days before administration (D-34);

TABLE 6-53

Influence of administrating tested substance for 30 days on mean platelet volume (Mean ± SD)

| Group | Animal No. | fe/m | Mean platelet volume MPV (fL) | | | | |
|---|---|---|---|---|---|---|---|
| | | | baseline[a] | D0 | D10 | D20 | D30 |
| GROUP A | 6890 | female | 8.5 | 8.5 | 7.9 | 7.9 | 8.4 |
| tested | 6642 | female | 9.1 | 8.7 | 8.0 | 8.9 | 8.3 |
| substance | 6500 | female | 8.0 | 8.4 | 8.3 | 7.6 | 7.9 |
| (3375 mg/kg) | Mean ± SD | | 8.5 ± 0.6 | 8.5 ± 0.2 | 8.1 ± 0.2 | 8.1 ± 0.7 | 8.2 ± 0.3 |
| n = 3 | | | | | | | |
| GROUP C | 6043 | male | 7.7 | 7.1 | 7.5 | 7.1 | 7.3 |
| placebo | 6343 | male | 9.1 | 9.7 | 8.5 | 9.9 | 9.2 |
| group | 6347 | male | 9.7 | 10.9 | 10.0 | 10.4 | 9.7 |
| n = 5 | 6872 | female | 8.5 | 8.2 | 9.5 | 9.8 | 9.5 |
| | 6880 | female | 7.9 | 8.6 | 8.7 | 8.0 | 8.5 |
| | Mean ± SD | | 8.6 ± 0.8 | 8.9 ± 1.5 | 8.8 ± 1.0 | 9.0 ± 1.4 | 8.8 ± 1.0 |

Notes:
1. [a]34 days before administration (D-34);

5.4 Conclusions

Under the conditions of this experiment, the dose of the tested substance was 15 times of the clinical equivalent dose for monkey, and 18 times of the pharmacodynamical (0.75 mg/kg mouse) equivalent dose for monkey (3375 mg/kg). After 30 days, no toxicity was observed in rhesus monkeys, indicating that the safety of the tested substance.

Example 7

In order to perform characterization and the quality control for the Traditional Chinese Medicine composition of the present disclosure, the inventor has established the fingerprint of the Traditional Chinese Medicine composition of the present disclosure by ultra-high performance liquid chromatography (UHPLC) after a lot of trials. The analysis conditions were as follows:

Instruments and reagents: Ultimate3000 liquid chromatograph system (Thermo) and Chromeleon 7.2 chromatography workstation, ultrapure water machine (molar 1810D cell type), ultrasound system (Jiemen JP-100ST).

Acetonitrile and methanol are chromatographically pure (Fisher) and formic acid is chromatographically pure (Fisher).

Preparation of test solution: the Traditional Chinese Medicine composition to be tested was weighed accurately, dissolved in 80° C. hot water, and subjected to ultrasonic extraction for 60 min; the supernatant was taken after centrifugation and filtered through 0.22 μm microporous membrane, and was formulated into 5 mg/mL solution.

Determination of fingerprint: 1 μL test solution was pipetted accurately into the ultra-high performance liquid chromatograph, and the chromatograms were recorded.

The operating conditions for the chromatography were as follows:
Column: Waters ACQUITY UPLC BEH C18 2.1×150 mm 1.7 μm column;
Mobile phase: mobile phase A: 0.05% formic acid in water, mobile phase B: acetonitrile;
Gradient elution:
0-18 min, 3% B-18% B; 18-23 min, 18% B-40% B; 23-28 min, 40% B-100% B; 28-30 min, 100% B-100% B; 30-32 min, 100% B-3% B;
Temperature: 25° C.;
Flow rate: 0.3 mL/min;
Detection wavelength: 254 nm;
Injection volume: 1 uL.

Figure 12:
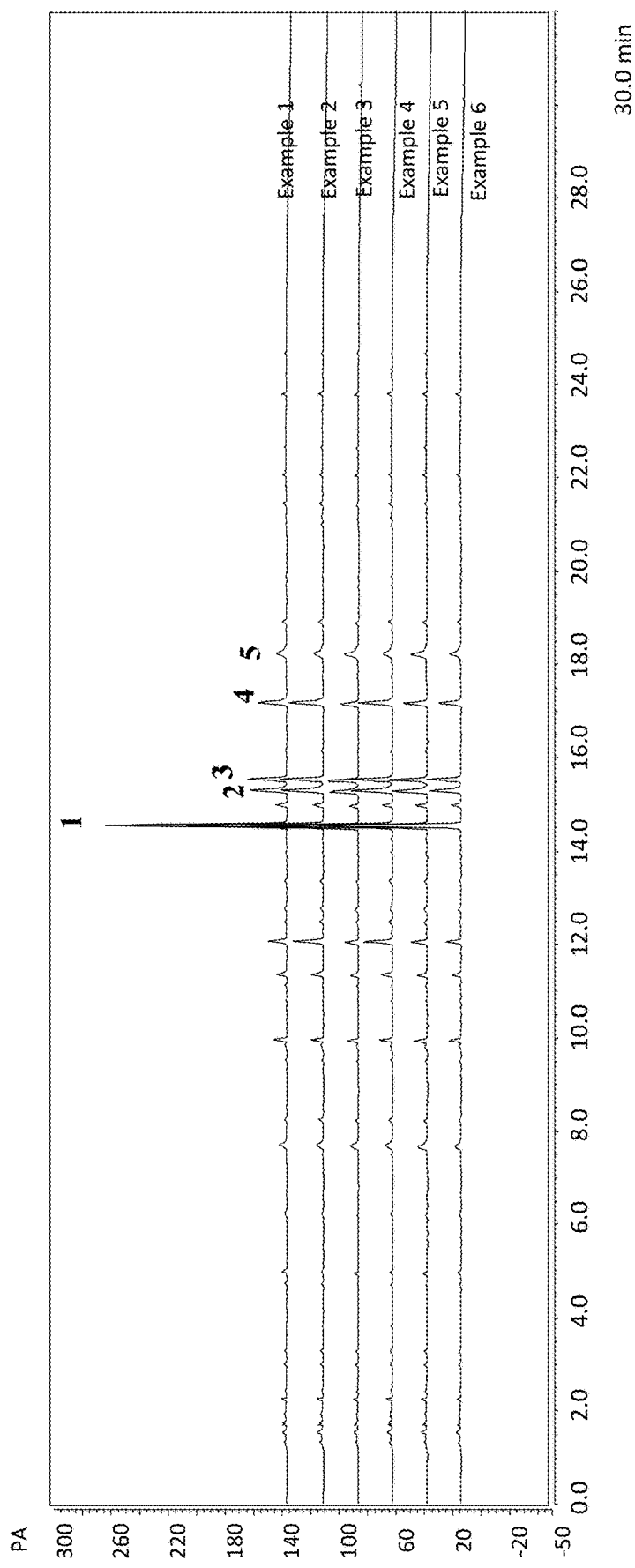
FIG. 12 shows the fingerprints of the Traditional Chinese Medicine composition of Examples 1-6.

The above chromatographic conditions were used for the UHPLC fingerprint analysis of the traditional Chinese medicinal compositions of Example 1 to Example 6. The spectra are shown in FIG. 12. The results show that the UHPLC spectra of the Traditional Chinese Medicine compositions of the present disclosure having the raw materials with amounts defined in the present disclosure have very good consistency, with five obvious characteristic peaks as shown in the Table below:

TABLE 7-1

UHPLC fingerprint data of the traditional Chinese medicinal compositions of Example 1 to Example 6

| | retention time, no. 1 peak (min) | retention time, no.2 peak (min) | retention time, no. 3 peak (min) | retention time, no.4 peak (min) | retention time, no. 5 peak (min) |
|---|---|---|---|---|---|
| Example 1 | 14.540 | 15.297 | 15.530 | 17.177 | 18.230 |
| Example 2 | 14.537 | 15.293 | 15.527 | 17.173 | 18.230 |
| Example 3 | 14.510 | 15.263 | 15.493 | 17.140 | 18.200 |
| Example 4 | 14.530 | 15.290 | 15.523 | 17.17 | 18.223 |
| Example 5 | 14.523 | 15.280 | 15.513 | 17.157 | 18.200 |
| Example 6 | 14.530 | 15.290 | 15.523 | 17.163 | 18.213 |

That is, the retention times of the five characteristic peaks (no. 1, 2, 3, 4, and 5) are about 14.5±0.1, 15.3±0.1, 15.5±0.1, 17.2±0.1, and 18.2±0.1 (min), respectively. Based on these characteristic peaks, the Traditional Chinese Medicine composition according to the present disclosure can be identified easily and they can also be used for quality control.

While the Examples have been described in detail hereinabove, it is understood that modifications and combinations may be made in the form and details without departing from the spirit of the present invention. It will be appreciated that, without departing from the disclosure and the claims as interpreted in broad sense, various changes may be made to the Examples described herein.

The invention claimed is:

1. A method for preparing an antiviral herbal medicine composition, comprising:

1) extracting Herba Taraxaci, Radix Stemonae and Radix Cynanchi Atrati by alcohol to give an alcohol extract;

2) combining the residues obtained during the preparation of the alcohol extract of step 1) with Radix Puerariae, Rhizoma Atractylodis Macrocephalae, and Pseudobulbus Cremastrae Seu Pleiones, extracting the mixture thus obtained by water, concentrating the extract liquid, causing precipitation in the concentrated extract liquid by adding an alcohol, and collecting the supernatant as a water extract; and 3) combining the alcohol extract obtained in step 1) and the water extract obtained in step 2) to obtain the antiviral herbal medicine composition after optional post processing;

wherein the amount of each of the raw material is as follows: Herba Taraxaci 30-70 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight.

2. The method of claim 1, wherein the alcohol is 40-95% ethanol solution in water.

3. The method of claim 1, wherein
the amount of Herba Taraxaci is 30-60 parts by weight, 35-55 parts by weight, or 40-50 parts by weight;
the amount of Radix Stemonae is 25-35 parts by weight, or 25-30 parts by weight;
the amount of Pseudobulbus Cremastrae Seu Pleiones is 25-35 parts by weight, or 25-30 parts by weight;
the amount of Radix Cynanchi Atrati is 20-45 parts by weight, 20-40 parts by weight, or 25-35 parts by weight;
the amount of Radix Puerariae is 20-45 parts by weight, 20-40 parts by weight, or 25-35 parts by weight; and
the amount of Rhizoma Atractylodis Macrocephalae is 20-55 parts by weight, 20-50 parts by weight, or 30-40 parts by weight.

4. The method of claim 1, comprising the following steps:
step 1), extracting Herba Taraxaci, Radix Stemonae, Radix Cynanchi Atrati and Cortex Mori by alcohol to give an alcohol extract, wherein the amount of Cortex Mori is 20-60 parts by weight, 20-55 parts by weight, 20-50 parts by weight, or 25-40 parts by weight; and
step 2), combining the residues obtained during the preparation of the alcohol extract of step 1) with Radix Puerariae, Rhizoma Atractylodis Macrocephalae, Pseudobulbus Cremastrae Seu Pleiones and Cortex Lycii, extracting the mixture thus obtained by water, concentrating the extract liquid, causing precipitation in the concentrated extract liquid by adding an alcohol, and collecting the supernatant as a water extract, wherein the amount of Cortex Lycii is 20-60 parts by weight, 20-55 parts by weight, 20-50 parts by weight, or 30-40 parts by weight.

5. An antiviral herbal medicine composition produced by a method comprising the following steps:
1) extracting Herba Taraxaci, Radix Stemonae and Radix Cynanchi Atrati by alcohol to give an alcohol extract;
2) combining the residues obtained during the preparation of the alcohol extract of step 1) with Radix Puerariae, Rhizoma Atractylodis Macrocephalae, and Pseudobulbus Cremastrae Seu Pleiones, extracting the mixture thus obtained by water, concentrating the extract liquid, causing precipitation in the concentrated extract liquid by adding an alcohol, and collecting the supernatant as a water extract; and 3) combining the alcohol extract obtained in step 1) and the water extract obtained in step 2) to obtain the antiviral herbal medicine composition after optional post processing;

wherein the amount of each of the raw material is as follows: Herba Taraxaci 30-70 parts by weight, Radix Stemonae 20-40 parts by weight, Pseudobulbus Cremastrae Seu Pleiones 20-40 parts by weight, Radix Cynanchi Atrati 20-50 parts by weight, Radix Puerariae 20-50 parts by weight, and Rhizoma Atractylodis Macrocephalae 20-60 parts by weight.

6. An oral pharmaceutical formulation comprising the herbal medicine composition according to claim 5 and a pharmaceutically acceptable carrier or adjuvant.

7. A method of treating or preventing a viral infectious disease or condition in a patient in need thereof, comprising orally administering to the patient an effective amount of the herbal medicine composition of claim 5; wherein the patient is a mammal.

8. The method of claim 7, wherein the viral infectious disease or condition is a disease or condition caused by Zika virus, dengue virus, or chikungunya virus, or a combination thereof.

9. The method of claim 7, wherein the viral infectious disease or condition is a disease or condition caused by influenza A virus.

10. The method of claim 7, wherein the mammal is a human being.

11. The antiviral herbal medicine composition of claim 5, wherein
the amount of Herba Taraxaci is 30-60 parts by weight, 35-55 parts by weight, or 40-50 parts by weight;
the amount of Radix Stemonae is 25-35 parts by weight, or 25-30 parts by weight;
the amount of Pseudobulbus Cremastrae Seu Pleiones is 25-35 parts by weight, or 25-30 parts by weight;
the amount of Radix Cynanchi Atrati is 20-45 parts by weight, 20-40 parts by weight, or 25-35 parts by weight;
the amount of Radix Puerariae is 20-45 parts by weight, 20-40 parts by weight, or 25-35 parts by weight; and
the amount of Rhizoma Atractylodis Macrocephalae is 20-55 parts by weight, 20-50 parts by weight, or 30-40 parts by weight.

12. The antiviral herbal medicine composition of claim 5, wherein Cortex Mori is additionally extracted in step 1), Cortex Lycii is additionally combined and extracted in step 2), and wherein the amount of Cortex Lycii is 20-60 parts by weight, 20-55 parts by weight, 20-50 parts by weight, or 30-40 parts by weight, and the amount of Cortex Mori is 20-60 parts by weight, 20-55 parts by weight, 20-50 parts by weight, or 25-40 parts by weight.

* * * * *

UNITED STATES PATENT AND TRADEMARK OFFICE
CERTIFICATE OF CORRECTION

PATENT NO. : 11,235,015 B2  
APPLICATION NO. : 16/613392  
DATED : February 1, 2022  
INVENTOR(S) : Hongzhang Jia Page 1 of 1

It is certified that error appears in the above-identified patent and that said Letters Patent is hereby corrected as shown below:

On the Title Page

Item (54) and in the Specification, Column 1, Line 1, replace "ANTIVIRAL TRADITIONAL CHINESE MEDICINE COMPOSITION AND PREPARATION METHOD AND USE I'HEREOF" with -- ANTIVIRAL TRADITIONAL CHINESE MEDICINE COMPOSITION AND PREPARATION METHOD AND USE THEREOF --.

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*